US012571020B2

(12) United States Patent
Bucci et al.

(10) Patent No.: US 12,571,020 B2
(45) Date of Patent: Mar. 10, 2026

(54) GENETICALLY ENGINEERED MICROORGANISMS THAT OVEREXPRESS MICROCIN-MGE AND METHODS OF PURIFICATION AND USE

(71) Applicant: University of Massachusetts, Boston, MA (US)

(72) Inventors: Vanni Bucci, Concord, MA (US); Benedikt M. Mortzfeld, Newton, MA (US); Jacob Palmer, Oxford (GB)

(73) Assignee: University of Massachusetts, Westborough, MA (US)

( * ) Notice: Subject to any disclaimer, the term of this patent is extended or adjusted under 35 U.S.C. 154(b) by 323 days.

(21) Appl. No.: 17/801,671

(22) PCT Filed: Feb. 23, 2021

(86) PCT No.: PCT/US2021/019225
§ 371 (c)(1),
(2) Date: Aug. 23, 2022

(87) PCT Pub. No.: WO2021/173545
PCT Pub. Date: Sep. 2, 2021

(65) Prior Publication Data
US 2023/0126514 A1 Apr. 27, 2023

Related U.S. Application Data

(60) Provisional application No. 62/980,921, filed on Feb. 24, 2020.

(51) Int. Cl.
| | |
|---|---|
| *C12P 21/00* | (2006.01) |
| *A61P 31/04* | (2006.01) |
| *C07K 14/245* | (2006.01) |
| *C12N 1/20* | (2006.01) |
| *C12N 15/70* | (2006.01) |
| *C12P 21/02* | (2006.01) |
| *A61K 38/00* | (2006.01) |

(52) U.S. Cl.
CPC .............. *C12P 21/02* (2013.01); *A61P 31/04* (2018.01); *C07K 14/245* (2013.01); *C12N 1/20* (2013.01); *C12N 15/70* (2013.01); *A61K 38/00* (2013.01); *C12N 2510/00* (2013.01); *C12N 2800/101* (2013.01)

(58) Field of Classification Search
CPC ........ C12P 21/02; A61P 31/04; C07K 14/245; C12N 1/20; C12N 15/70; C12N 2510/00; C12N 2800/101; A61K 38/00
See application file for complete search history.

(56) References Cited

U.S. PATENT DOCUMENTS

| | | |
|---|---|---|
| 11,560,543 B2 | 1/2023 | Bucci et al. |
| 2006/0269988 A1 | 11/2006 | Royer et al. |

| | | |
|---|---|---|
| 2015/0209393 A1 | 7/2015 | Wook et al. |
| 2020/0270569 A1 | 8/2020 | Bucci et al. |
| 2022/0218787 A1 | 7/2022 | Bucci et al. |

FOREIGN PATENT DOCUMENTS

| | | |
|---|---|---|
| WO | WO 2010/025267 | 3/2010 |
| WO | WO 2016/072936 | 5/2016 |
| WO | WO 2016/210373 | 12/2016 |
| WO | WO 2018/237198 | 12/2018 |
| WO | WO 2019/055781 | 3/2019 |

OTHER PUBLICATIONS

Palmer et al., "Microcin H47: A Class IIb Microcin with Potent Activity Against Multidrug Resistant Enterobacteriaceae", ACS Infect. Dis. 6:672-679, 2020 (Year: 2020).*
Vassiliadis G, Destoumieux-Garzón D Lombard C, Rebuffat S, Peduzzi J. (2010). Isolation and Characterization of Two Members of the Siderophore-Microcin Family, Microcins M and H47. Antimicrob Agents Chemother 54, No. 1.*
Thomas et al. (The Journal of Biological Chemistry. Vol. 279, No. 27, Issue of Jul. 2, 2004; pp. 28233-28242).*
Azpiroz et al., "Microcin H47 system: an *Escherichia coli* small genomic island with novel features," PLoS One, Oct. 11, 2011, 6(10):e26179, 7 pages.
Azpiroz et al., "Microcins and urovirulence in *Escherichia coli*. Microbial pathogenesis," Nov. 2009, 47(5):274-80.
Bayro et al., "Structure of antibacterial peptide microcin J25: a 21-residue lariat protoknot," Journal of the American Chemical Society, Oct. 13, 2003, 125(41):12382-3.
Bucci et al., "The evolution of bacteriocin production in bacterial biofilms," The American Naturalist, Dec. 1, 2011, 178(6):E162-73.
Chatham-Stephens et al., "Emergence of extensively drug-resistant *Salmonella typhi* infections among travelers to or from Pakistan—United States, 2016-2018," Morbidity and Mortality Weekly Report, Jan. 11, 2019, 68(1):11, 5 pages.
Daeffler et al., "Engineering bacterial thiosulfate and tetrathionate sensors for detecting gut inflammation," Molecular Systems Biology, Apr. 2017, 13(4):923, 13 pages.
David et al., "Epidemic of carbapenem-resistant Klebsiella pneumoniae in Europe is driven by nosocomial spread," Nature Microbiology, Nov. 2019, 4(11):1919-29.

(Continued)

*Primary Examiner* — Jeanette M Lieb
(74) *Attorney, Agent, or Firm* — Fish & Richardson P.C.

(57) ABSTRACT

This disclosure relates to genetically engineered microorganisms for overexpressing microcin compositions, e.g., MccH47 compositions and MccI47 compositions, which are post-translationally modified with a covalent linkage at the C-terminus to a siderophore, such as mono-glycosylated cyclic enterobactin (MGE), to form microcin-MGE compositions, e.g., MccH47-MGE and MccI47-MGE compositions, the purified compositions themselves, methods of making the purified compositions, and methods of using the purified compositions to treat or reduce the risk of bacterial infections or dysbiosis.

10 Claims, 8 Drawing Sheets

Specification includes a Sequence Listing.

(56) References Cited

OTHER PUBLICATIONS

Delgado et al., "YojI of *Escherichia coli* functions as a microcin J25 efflux pump," Journal of Bacteriology, May 15, 2005, 187(10):3465-70.

Duquesne et al., "Microcins, gene-encoded antibacterial peptides from enterobacteria," Natural Product Reports, 2007, 24(4):708-34.

EP European Search Report in European Appln. No. 18856596.4, dated Aug. 7, 2020, 17 pages.

EP European Search Report in European Appln. No. 20802507.2, dated Jun. 15, 2022, 9 pages.

EP Extended European Search Report in European Appln. No. 18856596.4, dated Nov. 10, 2020, 15 pages.

Fomenko et al., "Regulation of microcin C51 operon expression: the role of global regulators of transcription," Research in Microbiology, Jun. 1, 2001, 152(5):469-79.

Geldart et al., "pMPES: a modular peptide expression system for the delivery of antimicrobial peptides to the site of gastrointestinal infections using probiotics," Pharmaceuticals, Dec. 2016, 9(4):60, 16 pages.

Geldart et al., "pMPES: a modular peptide expression system for the delivery of antimicrobial peptides to the site of gastrointestinal infections using probiotics," Pharmaceuticals, Oct. 2, 2016, 9(4):60, 16 pages.

Gibson et al., "Enzymatic assembly of DNA molecules up to several hundred kilobases," Nature Methods, May 2009, 6(5):343-5.

Landry et al., "Engineering diagnostic and therapeutic gut bacteria," Microbiology Spectrum, Oct. 2017, 5(5), 22 pages.

Medina et al., "Tackling threats and future problems of multidrug-resistant bacteria," How to Overcome the Antibiotic Crisis, 2016, 3-33.

Mercado et al., "The production in vivo of microcin E492 with antibacterial activity depends on salmochelin and EntF," Journal of Bacteriology, Aug. 1, 2008, 190(15):5464-71.

Metelev et al., "Structure of microcin B-like compounds produced by Pseudomonas syringae and species specificity of their antibacterial action," Journal of Bacteriology, Sep. 15, 2013, 195(18):4129-37.

Mortzfeld et al., "MccI47 selectively inhibits enteric bacteria and reduces carbapenem-resistant Klebsiella pneumoniae colonization in vivo when administered via an engineered live biotherapeutic," bioRxiv, Jan. 1, 2021, vol. 2021, 22 pages.

Nadell et al., "Cutting through the complexity of cell collectives. Proceedings of the Royal Society B: Biological Sciences," Mar. 22, 2013, 280, 11 pages.

Ng et al., "Microbiota-liberated host sugars facilitate post-antibiotic expansion of enteric pathogens," Nature, Oct. 2013, 502(7469):96-9.

Nolan et al., "Biosynthetic tailoring of microcin E492m: post-translational modification affords an antibacterial siderophore-peptide conjugate," Journal of the American Chemical Society, Nov. 21, 2007, 129(46):14336-47.

Nolan et al., "Investigations of the MceIJ-catalyzed post-translational modification of the microcin E492 C-terminus: linkage of ribosomal and nonribosomal peptides to form "trojan horse" antibiotics," Biochemistry, Sep. 2, 2008, 47(35):9289-99.

Palmer et al., "Engineered probiotic for the inhibition of Salmonella via tetrathionate-induced production of microcin H47," ACS Infectious Diseases, Jan. 12, 2018, 4(1):39-45.

Patzer et al., "The colicin G, H and X determinants encode microcins M and H47, which might utilize the catecholate siderophore receptors FepA, Cir, Fiu and IroN," Microbiology, Sep. 1, 2003, 149(9):2557-70.

PCT International Preliminary Report on Patentability in International Appln. No. PCT/US2018/051079, dated Mar. 17, 2020, 9 pages.

PCT International Preliminary Report on Patentability in International Appln. No. PCT/US2020/031182, dated Nov. 2, 2021, 6 pages.

PCT International Preliminary Report on Patentability in International Appln. No. PCT/US2021/019225, dated Feb. 3, 2022, 11 pages.

PCT International Search Report and Written Opinion in International Appln. No. PCT/U20S18/051079 dated Feb. 7, 2019, 13 pages.

PCT International Search Report and Written Opinion in International Appln. No. PCT/US2020/031182, dated Aug. 18, 2020, 9 pages.

PCT International Search Report and Written Opinion in International Appln. No. PCT/US2021/019225, dated Aug. 10, 2021, 11 pages.

Poey et al., "Comparative analysis of chromosome-encoded microcins," Antimicrobial Agents and Chemotherapy, Apr. 1, 2006, 50(4):1411-8.

Poey et al., "Virulence profiles in uropathogenic *Escherichia coli* isolated from pregnant women and children with urinary tract abnormalities," Microbial Pathogenesis, May 1, 2012, 52(5):292-301.

Riglar et al., "Engineered bacteria can function in the mammalian gut long-term as live diagnostics of inflammation," Nature Biotechnology, Jul. 2017, 35(7):653-8.

Rodríguez et al., "The structural gene for microcin H47 encodes a peptide precursor with antibiotic activity," Antimicrobial Agents and Chemotherapy, Sep. 1, 1999, 43(9):2176-82.

Rojas et al., "Multidrug-Resistant Klebsiella pneumoniae ST307 in Traveler Returning from Puerto Rico to Dominican Republic," Emerging Infectious Diseases, Aug. 2019, 25(8):1583-5.

Sassone-Corsi et al.et al., Microcins Mediate Competition Among Enterobacteriaceae in the Inflamed Gut Naure; Dec. 8, 2016; vol. 540, 25 pages.

Vassiliadis et al., "Isolation and characterization of two members of the siderophore-microcin family, microcins M and H47," Antimicrobial Agents and Chemotherapy, Jan. 2010, 54(1):288-97.

Winter et al., "Gut inflammation provides a respiratory electron acceptor for *Salmonella*," Nature, Sep. 2010, 467(7314):426-9.

Winter et al., "Host-derived nitrate boosts growth of *E. coli* in the inflamed gut," Science, Feb. 8, 2013, 339(6120):708-11, 5 pages.

Bantysh et al., "Enzymatic synthesis of bioinformatically predicted microcin C-like compounds encoded by diverse bacteria," Mbio, Jul. 2014, 5(3):10, 11 pages.

EP Extended European Search Report in European Appln. No. 21760771.2, mailed on Mar. 14, 2024, 11 pages.

Gaggero et al., "Genetic analysis of microcin H47 antibiotic system," Journal of Bacteriology, Sep. 1993, 175(17):5420-7.

* cited by examiner

*multi-drug resistant isolate

SEQUENCE LISTING

```
<160> NUMBER OF SEQ ID NOS: 15

<210> SEQ ID NO 1
<211> LENGTH: 1119
<212> TYPE: DNA
<213> ORGANISM: Escherichia coli

<400> SEQUENCE: 1
atgcgaaaac gtattctttt tattggccca ccgctgtacg gtttgttata cccattgatt      60
tctctggctc aggcctttcg tgtaatcgga catgatgtag taattagtag tgctggcaaa     120
ttcgcgaata aagcagcaga agctggactg gttgtttttg atgcagttcc aggtttagat     180
tcagaggctg gatatcgcca tcaggaagag ttgaggaaaa aaagtaatat tattggtcat     240
ttctcttttt ttagcgatga aatggcagat aacctcatcg attttgcagg aaaatggagg     300
ccagatttaa tagtctatcc cccgcttggt ccggcaggcc cattggttgc tgctaaatat     360
```

-continued

```
agaattcctt cagtgatgct ggctgttgga ttcgcgcata catctgccca tattcagatg    420
ttaaaccgtt ctttaagcaa tgcttacagg cggcatggag tcagcggtcc actatgtgat    480
ttagcatgga ttgatgttgc tcccccaagt atgagcattc ttaaaaatgc tgaagaaccg    540
gttatctcaa tgagatatat tccttataac ggaggtgctg taaaggaaac atggtgggac    600
agggattctg atcgaaaacg tttactcatc agccttggca ctgtaaaacc aatggttgat    660
ggtctggagc tgatttcatg ggttatggat tctgcaaatg aagttgatgc tgatatcatt    720
ttgcaacttg caataaatgc tcgtactgga ttacgaaaac taccatcaaa tgtacgtctg    780
gttgactgga tacctatggg tgtattcctt aatggagctg atggatttat tcatcatggt    840
ggcgcaggta ataccctgac agcgttgtat agtgggatac cacagattgt gtttggcgaa    900
ggtgcagatc gctctgttaa tgcagaaatt gttgcgatgc gtgggtgtgg gattattccg    960
gacaagcatg gactgaccag tgatttggta aatcgcctgc tttatgatga ttcactacgc    1020
ttctgttcag atcaggtagc cgctgaaatg gctgaacaac ccagtcctgc agagatcgca    1080
gaggttttga tgagaaaatt aaaaaacaac gggaaataa                            1119
```

<210> SEQ ID NO 2
<211> LENGTH: 1551
<212> TYPE: DNA
<213> ORGANISM: Escherichia coli

<400> SEQUENCE: 2

```
atgagtcatc agtgttcact ttctgaactg aatgaaaacc tggtgccttt cactgccagg     60
cagatcaagt cctcattaat ctggtgtgca gaggatgtca gaaatccagg cgagctgcaa    120
aatgcctgca gttatattat cgatcctgac agtacggctt ctgccaaagt gttccatgca    180
gagcgctatg gtggcagtgg tattcagcgt aatggaggtg gtgcacgttg tgggtttgat    240
ggtaactacc aggttaaagg aataggaagt aatccgttgg ttggtgaagg tactgacgaa    300
cgtcattcta atggtgcact cggcgctgtt catgcaatat atgaggcttt gtggggagaa    360
gtactggctc aaatattacc ttatagtgct gtgcgggttc gggcggtttt acttacagat    420
ctctatactg aaaaggcatt tgagcgctcc ggtatgaaat cacgaagagc cctgttggta    480
cgtgagcctg ttgttcgccc ggcgcatttt gaacgggcac atacttcca agtaaaaccg     540 gagtattcca gtcagttaat tcacgatgcc tgtcgggtta gatctgtgat ccacaagctg    600
ccaggatatc tacctgtacc accggaagaa attgatgctg aagcacgaac tgatccccgg    660
atttattgca ttgagggatt atgtgaactg gcacgtcgtg aggcctggca aatggcattt    720
tgtcgaacac gtttcctgag attgacaact ctccttcta atattgcaat ggatggcaga    780
ttaatggatt ttaacggact cagttgctcg tttccgggga attccccagc tgattttggg    840
tataaactaa gattagctga actggcaaaa gaaccgatgg tacttatgca agggctgtct    900
gatctctgct gtatatcgg aaaatatatg tttgaccctg acttcactct gcagccccgt     960
ttgaaggttg aggagatatt tcagaaaact tttcatgaag catgttatta ctgttatcta    1020
gaactgttgg gtattcctgg agaatttata acacaaaaag agatacctga tatattgaaa    1080
caactggtta acagttttgt tgcattactc aataaatact gcgagaaatc acatgcccaa    1140
gatattgtca atcaggatgg ttcaccattg caaaagttgg ttgtgacgct aatccatcat    1200
aggcataatc aaaagcaggc actgaatagt agcatcaaga tgatgtttta tttcaccgtt    1260
gcacaacagt gttttttccca gactatccac tggctgacgc aaggcagtac cagacgtcag    1320
```

-continued

```
ataaatgctt cattactcct gaaagaaatt gaacatcata ccatgaaaag gctgcaaccc      1380
agggaagagc tgaggaaaga gaatatgtgc gaaaaaattg ccatcctgct ggataatcat      1440
ggcgatgatc ccctttttt acaagaagca atttctgata tgaaaaattt tatgcttaag       1500
ttttccagag atgcatttgg atatcttgaa ccgataagaa acacagtgta a               1551

<210> SEQ ID NO 3
<211> LENGTH: 453
<212> TYPE: DNA
<213> ORGANISM: Escherichia coli

<400> SEQUENCE: 3
atgtcttata taagggaaac catcagagga aaagatgaat ggactgttta tgaacagata        60
ggttttgcgg tcagttgtat gctctacaat cgtaattaca gtctgtatcc ggtgttaacc       120
attcaatact ggactgaata tgcgatacag cataatcaga ttaaattcct gtttgattca       180 cgaggtttc cactggcgta tataacctgg gcatatcttg aggctgatac ggaagcgcgc        240
ctgctcaggg atccagaatt caggttgcat ccgtctgaat ggaatgaaga tggaaggatc       300
tggatcctgg atttctgttg taaaccaggc tttggtcgaa aagttattga ctatctcata       360
cagcttcagc catggggggga aggagaagta cgatggttaa gcaggcgaaa gaaaattgtg      420
acatacatcc ctgagcggct gcataaaacg tag                                    453

<210> SEQ ID NO 4
<211> LENGTH: 228
<212> TYPE: DNA
<213> ORGANISM: Escherichia coli

<400> SEQUENCE: 4
atgcgagaaa taacagaatc acagttaaga tatatttccg gggcgggagg tgcgccagcg        60
acttcagcta atgccgcagg tgctgcagct attgttggag ctctcgccgg aatacctggt       120
ggtccacttg gggttgtagt tggagccgta tctgccggtt tgacaacagc aattggctcg       180
accgtgggaa gtggtagtgc cagttcttct gctggtggcg gtagctaa                    228

<210> SEQ ID NO 5
<211> LENGTH: 1275
<212> TYPE: DNA
<213> ORGANISM: Escherichia coli

<400> SEQUENCE: 5
ttgtttcgtc aggatgcttt agaaaacaga aaaatgaagt ggcagggacg ggcaatatta        60
cttcccggaa taccactatg gttaatcatg ctgggaagca ttgtgtttat tacggcattt       120
ctgatgttca ttattgttgg tacctatagc cgccgtgtta atgtcagtgg tgaggtcaca       180
acctggccaa gagctgtcaa tatatattca ggtgtacagg gatttgttgt caggcaattt       240
gttcatgaag ggcagttgat aaaaaaaggg gatcctgttt atctgattga catcagtaaa       300
agtacacgta gtggtattgt cactgataat catcggcggg atatagaaaa tcagctggtt       360
cgtgtggaca acattatttc ccgtctggaa gaaagtaaaa aaataacgtt agataccctg       420
gaaaaacaac gtctgcaata cacagatgcg tttcgtcgct catcagatat tatacagcgt       480
gcagaggaag ggataaaaat aatgaaaaac aatatggaga attacagaaa ctatcaggca       540
aaagggctga ttaataaaga tcagttaact aaccaggtgg cattatatta tcagcaacaa       600
aacaatcttc tcagcctgag cggacagaac gaacagaatg ccctgcagat aaccactctg       660
gagagtcaga ttcagactca ggctgcagat tttgataacc gtatctacca gatggaactg       720
```

-continued

```
caacggtacg agttacagaa agaactggtt aacactgatg tggagggcga aattattatc      780
cgggcgttga ctgacgggaa agttgactcc ctgagtgtca ctgtcgggca aatggtcaat      840
accggagaca gccttctgca ggttattcct gagaacattg aaaactatta tcttattctc      900
tgggtcccaa atgatgctgt tccttatatt tcggctggtg acaaagtgaa tattcgttat      960
gaagcctttc cggcagaaaa atttgggcag ttctctgcta cggttaaaac tatatccagg     1020
actcctgcgt caacacagga aatgttgacc tataagggtg caccacagaa tacgccgggc     1080
gcctctgttc cctggtataa agtcattgcg atgcctgaaa agcagattat cagatatgac     1140
gaaaaatacc tccctctgga aaatggaatg aaagccgaaa gtacactatt tctggaaaaa     1200
aggcgtattt accagtggat gctttctcct ttctatgaca tgaaacacag tgcaacagga     1260
ccgctcaatg actaa                                                       1275

<210> SEQ ID NO 6
<211> LENGTH: 2097
<212> TYPE: DNA
<213> ORGANISM: Escherichia coli

<400> SEQUENCE: 6
atgactaacg ggagtttcag acaaattata aatcagcttg atatgcgctg gcgacgtcgt       60
gttccggtta ttcatcagac ggagaccgct gaatgtggac tggcctgcct ggcaatgata      120
tgcggtcatt ttggtaagaa tattgacctg atatctcttc gccggaagtt taatctctcg      180
gcccgtggag caaaccttgc aggaatcaat ggaatagcgg agcagctggg gatggtcacc      240
cgggctcttt cactggagct ggatgaactt ggtgccctca aaatgccgtg tattctccac      300
tgggatttca gtcactttgt cgtgctggtc agcgtaaagc gtaaccgtta tgtactgcat      360
gatccggcca gaggcagaag atatctcggt cgggaggaaa tgagccggta ttttacgggc      420
attgcacttg aggtctggcc tggaagtgaa ttcctggcgg aaacccagca gatccgcata      480
agtctccgtt cactgattaa cagtatttac ggtattaaaa gaacactggc gaaaattttc      540
tgtctgtcag ttgtaattga agcaatcaat ctggtaatgc cggtggggac tcagctggtt      600
atggatcatg cgattccggc gggggacaga gggctgctga cgcttatttc tgctggcctg      660
atgttcttta tattgctcag ggccgcggtg agtatgctgc gtgcatggtc ctcactggtt      720
atgagcacgc tcatcaatat acagtggcag tcgggtctgt ttaaccatct tctcagactg      780
ccgctggcgt tttttgaacg ccgtaaatta ggtgatatcc agtcgcgttt tggctccctt      840
gacactttga gggccacctt taccacctgt gtggttgggg caatcatgga cagtattatg      900
gttgtggggg tttttgtgat gatgctgtta tatggaggat atcttacctg gatagtgctc      960
ggttttacca tggtttacgt tcttattcgt ctggtgacac acggctatta ccggcaaata     1020
tcggaagaaa ctcttgtcag gggggcccgg gccagctcct attttatgga aagcctgtat     1080
ggtattgcca cggtaaaaat ccaaggtatg gctgggatcc ggggaacaca ctggcttaac     1140
ctgaaaatag atgcgatcaa ttcaggtatt aagttaacca agatggattt gctcttcggg     1200
gggataaata cttttgttgc cgcctgtgat caggtggcga ttttatggct gggtgcaagc     1260
cttgtgatcg ataatcagat gacaataggg atgtttgtgg catttggttc ttttcgtggg     1320
cagttttcgg atcgggttgc ttcgctgacc agtttttctt ttcaactgag aataatgagt     1380
ctgcataatg agcgcattgc agatattgca ctacatgaaa aggaagaaaa gaaaccggaa     1440
attgaaatcg ttgctgacat gagcccggtt tcactggaaa ccactgattt aagctaccgg     1500
```

-continued

```
tatgacagcc agtcagcaca ggtattcagt ggtctgaatt tgtctgtggc tccgggagaa    1560
agtgtggcta taactggtgc ctccggtgcc ggaaaaacca cattaatgaa agtattatgt    1620
ggactgtttg aaccagatag tggaaaagta ctggttaatg gcacggatat acgtcaactt    1680
ggaataaata attatcaccg tatgatagcc tgtgttatgc aggacgaccg gctattttca    1740
ggatcaattc gtgaaaatat ctgtgggttt gcagaagaaa cagacgacga atggatgaca    1800
gaatgtgcca gagcaagtca tattcatgat gtgataatga aaatgccaat ggggtatgaa    1860
acgttaatag gtgaactggg ggaaggtctt tccggcggtc aaaaacagcg tatattcatt    1920
gcccgagctt tataccggaa acctggaata ttatttatgg atgaggctac aagttctctt    1980
gatacagaaa gtgaacgttt cgtgaatgct gccataaaaa aaatgaatat cacccgggtg    2040
attattgcac acagagaaac tacgttgaga actgttgaca ggattatttc tatttaa      2097
```

<210> SEQ ID NO 7
<211> LENGTH: 210
<212> TYPE: DNA
<213> ORGANISM: Escherichia coli

<400> SEQUENCE: 7

```
atgagttata aaaaactgta ccaattgacg gctatattta gtttacctct tactatctta      60
ttggtttcac tttcatccct tcggattgtt ggcgaaggga attcttatgt tgacgttttt     120
ctaagcttta taatatttct tggtttattt gagctgattc atgggattcg aaagattttg     180
gtctggtcag gctggaaaaa cggaagttaa                                      210
```

<210> SEQ ID NO 8
<211> LENGTH: 120
<212> TYPE: DNA
<213> ORGANISM: Escherichia coli

<400> SEQUENCE: 8

```
atggaatttg ctacaaacag ggttactgta aatgacagtc ggtcagcact gtcatcaact      60
ttgctgttgt ctttgatcat gagcgccact ctactggaat attctttatc gatgacctga     120
```

<210> SEQ ID NO 9
<211> LENGTH: 1266
<212> TYPE: DNA
<213> ORGANISM: Escherichia coli

<400> SEQUENCE: 9

```
atgaaaaact atctttttcca gactcccgaa gatatttgtg tacagttaaa aaaaatgaca      60
catcctgtca caataagaac aacagatatt gctaatttct ggcactatct tgagtcagca     120
actcttccgg tgatcacaaa aagcaccact acagaaaatc gggaggttac atttctgtgg     180
cgctcagaga aagcagtgca aggcgtatat cttcgcctga tcgtgttac agataaaaaaa     240 gatgtcaaaa aaggactaat gactcatatc ccttcgacag atatctggat gctgacactg     300
gtgttaccag cttcatatcg gggctcatac tcatttatag aaattcccac agatatgaca     360
caaaaagaca tatttcaact aggaagtcgc ttctctccat acccggtaa atctgatcca      420 tttaacaaaa cagcagaaat aaatatacga ggattcggag aatcagtcct ttctcttgat     480
atggctcctg aacaaaagga atgggatgat acttcccata aatgtacagg tattctttca     540
acattacatt cctttgttgc aggatatcaa cgccggattc gtttatattt tccccagaat     600
ccaacatcag tacctcttgg attacttgtg ttacctgatg ctgaaatatg gtttgaccgg     660
atggatatta cccgggcatt agatatggcc attaccactg gtcatattgc gccaatggca     720
```

-continued

```
attatgggga tagacaatat taatgaatct gatcgtatga atatactggg aggcaataaa      780
gaacttatct ttgatatagc ggaaaatctg atacccagt tatacagaga ctacccgaat       840
atcgtatggg ctggtcgttc taatactata ctggccggtc agagcctcgg tggagtgaca      900
gcactgatgg cagctatata tgcgtcgaca acatttggta caatcattag ccactcacct      960
tcaatgtggt ggaaccctga ccagggcagc ccgattttgt ttactgagaa tgatatctcc     1020
tgggtaagtg agcagatact ttcagcgcct ccgaaagatg taaatatcca acttggagtc     1080
ggttctttag aaggtacaac cgtctcacat gttcagcggt tgcatcagtc gttaatcgca     1140
gcaggtttgg aaagtaacct cactgtctat gccggtggtc atgattatgc ctggtggcgc     1200
ggagcaatta ttgatgcatt agcaaattat aattgcagga agatatcaga taataacttt     1260
gtgtaa                                                                 1266

<210> SEQ ID NO 10
<211> LENGTH: 246
<212> TYPE: DNA
<213> ORGANISM: Escherichia coli

<400> SEQUENCE: 10
atgaattgtg ataataatca cagaaatgaa gaattcattg ttacctttga taaaggcaac       60
aagcaagaca attcaagacg aaaacacgat aattttccta tagaggtaga atcctccgta      120
gagctggaga cacactgtat cacaaataat aagtcggctt ccggtatagt aacacatgac      180
tatgatgccg attatatttg tggttgtggt gaaattatgt gtcctggttg cggtcatgac      240
ctataa                                                                 246

<210> SEQ ID NO 11
<211> LENGTH: 234
<212> TYPE: DNA
<213> ORGANISM: Escherichia coli

<400> SEQUENCE: 11
atgagagaaa tatcagataa catgcttgat tccgtgaaag gagggatgaa tcttaatgga       60
ttacctgctt ctactaatgt aatagatcta cgtggaaaag atatgggaac atatattgat      120
gctaatggag catgctgggc tccggatact ccatccatca tcatgtatcc gggggggaagt      180 ggaccttctt atagtatgag tagttccaca tccagtgcaa acagcggcag ttaa            234

<210> SEQ ID NO 12
<211> LENGTH: 435
<212> TYPE: DNA
<213> ORGANISM: Escherichia coli

<400> SEQUENCE: 12
atgtatctta cgaaaaagat tataataagt atgatgttta tattaccatc tgctgcattt       60
tcatcagatc cacctcccct tcaacaatcg ttagaaaaaa caacctattt ttctataggt      120
atgaatgggt ttataggcta tcagagcgaa ggggaaaaat tatacacaca cattcttaca      180
ttagataatc ccgaagagat atttaaaaat ataataaaaa atagaaagtc aactaaggag      240
tctaaaattt atgctgcttg tgggctatat tatttaaacg tagaaaatat agagtcattg      300
tttaatgaaa atgataaaca agaatatgtg tctgtcttaa gagggggatat tttaacaaaa      360 ataaaactga atgatattct gaattctgtg ataataaatg gttgcaacac caaattaata      420
tctgaacata aatga                                                       435
```

```
<210> SEQ ID NO 13
<211> LENGTH: 122
<212> TYPE: DNA
<213> ORGANISM: artificial
<220> FEATURE:
<223> OTHER INFORMATION: pBAD promoter sequence

<400> SEQUENCE: 13
ccacaattca gcaaattgtg aacatcatca cgttcatctt tccctggttg ccaatggccc      60
attttcctgt cagtaacgag aaggtcgcgt attcaggcgc tttttagact ggtcgtaatg     120
aa                                                                     122

<210> SEQ ID NO 14
<211> LENGTH: 163
<212> TYPE: DNA
<213> ORGANISM: artificial
<220> FEATURE:
<223> OTHER INFORMATION: Pttr promoter sequence

<400> SEQUENCE: 14
cccaatatcc ctgtcaatta tgttgtttta gatcaacaac aagccgggta tgtggttaac      60
cacaatagag cgcaccccgc ctcgattttt acactgtaaa tcatcgacat tttttattca     120
ttacacatga accaacatcg tgacaaatgt ttcattgttg gca                       163

<210> SEQ ID NO 15
<211> LENGTH: 34
<212> TYPE: DNA
<213> ORGANISM: artificial
<220> FEATURE:
<223> OTHER INFORMATION: J23110 promoter sequence

<400> SEQUENCE: 15
ttgacagcta gctcagtcct aggtataatg ctag                                  34
```

GENETICALLY ENGINEERED MICROORGANISMS THAT OVEREXPRESS MICROCIN-MGE AND METHODS OF PURIFICATION AND USE

CLAIM OF PRIORITY

This application is a U.S. National Stage Application of International Application No. PCT/US2021/019225, filed on Feb. 23, 2021, which claims the benefit of U.S. Provisional Patent Application Ser. No. 62/980,921, filed on Feb. 24, 2020. The entire contents of the foregoing applications are hereby incorporated by reference.

FEDERALLY SPONSORED RESEARCH OR DEVELOPMENT

This invention was made with Government support under Grant Nos. DBI1458347 and 1817342 awarded by National Science Foundation and Grant No. AI112985 awarded by the National Institutes of Health. The Government has certain rights to the invention.

SEQUENCE LISTING

This application contains a Sequence Listing that has been submitted electronically as an ASCII text file named Sequence_Listing.txt. The ASCII text file, updated on Aug. 12, 2022, is 14,539 bytes in size. The material in the ASCII text file is hereby incorporated by reference in its entirety.

TECHNICAL FIELD

This disclosure relates to genetically engineered microorganisms and methods of use.

BACKGROUND

Medical complications related to multi-drug resistant (MDR) and extensively drug resistant (XDR) bacteria, including those from the Enterobacteriaceae (mainly *Klebsiella, Salmonella, Shigella* and *Escherichia coli*) are a major issue in modern healthcare due to the increased morbidity, mortality, length of hospitalization and related healthcare costs.[1] New report from CDC on antimicrobial resistance threat shows that 500,000 hospitalization and 50,000 deaths are associated with antibiotic resistance every year (CDC's Antibiotic Resistance (AR) Threats Report, 2019). Every year more than two million people acquire MDR infections, which result in over 23,000 directly related deaths and several more lethal outcomes from associated complications.[2] The gastrointestinal tract is both the locus of infection and the reservoir of resistance for several enteric pathogens, including XDR *Salmonella typhi*,[3] and recent work has demonstrated microbiota-mediated colonization resistance to *Salmonella* infection.[4] Therefore, proteins and metabolites produced by gut commensal bacteria have become a major target for the discovery of new drugs to cure infections and prevent colonization by MDR/XDR pathogens.[5]

For example, prokaryotic antimicrobial peptides are abundant in nature, and serve as a type of chemical warfare with neighboring cells.[6,7] While small molecule antimicrobials produced by bacteria have been exploited for decades as traditional antibiotics, antimicrobial peptides as therapeutic agents have just recently gained widespread interest as potential treatments for MDR and XDR human pathogens.[8,9]

Of these antimicrobial peptides, microcin H47 (MccH47), an antimicrobial peptide produced by some strains of *E. coli*, e.g., strain Nissle 1917 (EcN), has gained significant recent interest. However, in contrast to other microcins, MccH47 has been particularly difficult to purify and most efforts to determine inhibitory activity have utilized live-producing strains via a variety of methodologies.[10-12] This has resulted in conflicting reports of MccH47's efficacy in regards to inhibitory activity of *Salmonella*, with some studies reporting inhibition,[10,11,13] and others reporting no inhibition.[14,15] In 1990, Laviña et. al. made the sole claim of MccH47 activity against additional members of the Enterobacteriaceae family,[13] yet no data were provided. Notably, MccH47 has never been purified to homogeneity[6] and Vassiliadis et al. were unable to detect inhibitory activity against targets other than *E. coli*.[14]

Another microcin, MccI47, is produced by genes in the same *E. coli* gene cluster as microcin H47 and sequence analysis revealed that it follows structural features know from other class IIb microcins.[16] MccI47 expression could be detected in iron deprivation conditions[17] in vitro. However, this microcin has not been described as having been overexpressed heterologously or described as having antimicrobial activity against bacteria.

SUMMARY

The present disclosure provides compositions of genetically engineered, and non-naturally occurring microorganisms to overexpress new forms of microcin, e.g., MccH47 and MccI47, which are post-translationally modified with a covalent linkage at the C-terminus to a siderophore such as mono-glycosylated cyclic enterobactin (MGE) to form microcin-MGE compositions, such as MccH47-MGE and MccI47-MGE compositions, which are not found in nature. Applicants are the first to have isolated and purified this particular form of the MccH47 and MccI47 microcins, enabling lyophilization and/or encapsulation of these microcins for administration, e.g., oral administration, e.g., in powdered or tablet form, which avoids the need to administer genetically modified bacteria. All prior descriptions of these microcins have been of mixtures of different forms of microcin, or live bacteria producing these mixtures.

In one aspect, provided herein is an isolated and purified microcin-mono-glycosylated cyclic enterobactin (MGE) composition.

In some embodiments, the microcin-MGE composition comprises a class IIb microcin-MGE composition.

In some embodiments, the microcin-MGE composition comprises an MccH47-MGE, MccI47-MGE, MccE492-MGE, MccM-MGE, or MccG492-MGE composition.

In some embodiments, the microcin-MGE is post-translationally modified with a covalent linkage at the C-terminus to the MGE.

In some embodiments, the microcin-MGE composition comprises an MccH47-MGE composition or an MccI47-MGE composition.

In some embodiments, the composition provided herein further comprises a pharmaceutically acceptable carrier.

In some embodiments, the pharmaceutically acceptable carrier comprises one or more of a solvent, dispersion media, coating, antibacterial agent, isotonic and absorption delaying agent, buffer, excipient, binder, lubricant, gel, or a surfactant.

In some embodiments, the composition provided herein is formulated for use in a method of treating a subject for a bacterial infection.

In some embodiments, the composition provided herein is formulated for use in a method of treating a subject for dysbiosis.

In another aspect, provided herein is a genetically engineered microorganism capable of producing a microcin-MGE composition, wherein the microorganism comprises a microcin operon, and a controllable promoter for the microcin operon, wherein the microcin operon comprises mciI, mciA, mchC, mchD, mchE, and mchF, or mchB, mchI, mchX, mchC, mchD, mchE, and mchF, but does not include a gene that encodes enterobactin esterase or a enterochelin esterase homolog, e.g., genes mchS1 or mchS4; wherein the controllable promoter controls a level of expression of the one or more microcin genes, thereby controlling the amount of microcin produced by the genetically engineered microorganism, and wherein either or both of the microcin operon and the controllable promoter are heterologous to the microorganism.

In some embodiments, the genetically engineered microorganism is a bacterium.

In some embodiments, the genetically engineered microorganism is *Escherichia coli.*

In some embodiments, the microorganism provided herein further comprises a second microcin operon comprising mchA and a controllable promoter for the second microcin operon, wherein the controllable promoter controls a level of expression of the one or more microcin genes, thereby controlling the amount of microcin produced by the genetically engineered microorganism.

In some embodiments, the controllable promoter is apJ23119 promoter.

In some embodiments, the one or more microcin operons and the one or more controllable promoters are in the genome of the microorganism.

In some embodiments, the one or more microcin operons and the one or more controllable promoters are in a vector.

In another aspect, provided herein is a composition formulated for use in treating a bacterial infection or dysbiosis, wherein the composition comprises any one of the genetically engineered microorganisms provided herein.

In some embodiments, the composition is packaged in a capsule for intestinal delivery.

In some embodiments, the bacterial infection is a gram-negative bacterial infection.

In some embodiments, the bacterial infection is carbapenem-resistant Enterobacteriaceae infection, *Campylobacter* infection, *E. coli* infection, *Salmonella* infection, *Shigella* infection, and/or *Yersinia* infection.

In another aspect, provided herein is a method of treating intestinal dysbiosis, the method comprising: identifying a subject as having intestinal dysbiosis; and administering to the subject a therapeutically effective amount of any one of the microcin-MGE compositions provided herein or any one of the genetically engineered microorganisms provided herein, or any one of the compositions provided herein.

In some embodiments, the subject is a human and the composition is administered by endoscopy, enteroscopy, colonoscopy, a nasoduodenal catheter, enema, or by oral administration.

In some embodiments, the composition is orally administered, e.g., in a capsule.

In another aspect, provided herein is a method of treating a bacterial infection, the method comprising: identifying a subject as having a bacterial infection; and administering to the subject a therapeutically effective amount of any one of the microcin-MGE compositions provided herein or any one of the genetically engineered microorganisms provided herein, or any one of the compositions provided herein.

In some embodiments, the subject is a human and the composition is administered by endoscopy, enteroscopy, colonoscopy, a nasoduodenal catheter, enema, or by oral administration.

In some embodiments, the composition is orally administered, e.g., in a capsule.

In some embodiments, the bacterial infection is a gram-negative bacterial infection.

In some embodiments, the bacterial infection is carbapenem-resistant Enterobacteriaceae infection, *Campylobacter* infection, *E. coli* infection, *Salmonella* infection, *Shigella* infection and/or *Yersinia* infection.

In another aspect, provided herein is a method of reducing a risk of a bacterial infection, the method comprising: identifying a subject as having a risk of a bacterial infection; and administering to the subject a prophylactically effective amount of any one of the microcin-MGE compositions provided herein or any one of the genetically engineered microorganisms provided herein, or any one of the compositions provided herein.

In some embodiments, the subject is being administered one or more antibiotics.

In some embodiments, the subject is a human and the composition is administered by endoscopy, enteroscopy, colonoscopy, a nasoduodenal catheter, enema, or by oral administration.

In some embodiments, the composition is orally administered, e.g., in a capsule.

In another aspect, provided herein is a method of producing a purified microcin-MGE composition, the method comprising: obtaining a genetically engineered microorganism capable of producing any one of the microcin-MGE composition provided herein; growing the microorganism, e.g., under antibiotic selection (e.g., with ampicillin and/or chloramphenicol) and/or, e.g., under iron-limiting conditions to maximize enterobactin production; growing for an additional time, e.g., for about 5-7 hours, post-induction; pelleting and freezing the microorganisms overnight, e.g., at about −20° C.; thawing the pellets in cold water and sonicating to form a crude lysate; passing the crude lysate through a column, e.g., an amylose resin column, to capture maltose binding protein (MBP) fusion proteins; eluting with maltose by adding an elution buffer, discarding, e.g., the first about 5 mL, and then capturing, e.g., the next 30 mL, as an eluent; concentrating the eluent, digesting by adding an endopeptidase to form a digestion mixture, and incubating, e.g., overnight, e.g., at 4° C.; raising the temperature of the digestion mixture, e.g., to room temperature, adding an additional amount of the endopeptidase, and optionally incubating an additional about 1-2 hours to yield a buffered solution of microcin (e.g., MccH47), endopeptidase, and MBP; further purifying the buffered solution, e.g., by subsequent rounds of resuspension with Ni-NTA agarose resin, to form a slurry; and pelleting the slurry by centrifugation, and removing the purified microcin (e.g., MccH47) in the supernatant by pipetting.

In some embodiments, growing the microorganism further comprises adding 0.2 mM 2'2-dipyridyl and inducing with 0.5 mM IPTG when cultures reached an optical density at 600 nm (OD600) of approximately 0.2.

In some embodiments, the elution buffer comprises 200 mM NaCl, 20 mM Tris-HCl, 10 mM maltose; pH 7.5.

In some embodiments, the eluent is concentrated using a 10,000 MWCO filter.

In some embodiments, the endopeptidase comprises a Tobacco etch virus nuclear-inclusion-a endopeptidase.

In another aspect, the disclosure provides methods of isolating and purifying the new microcins, as well as methods of use of the purified microcin-MGE compositions for treating bacterial infections and dysbiosis. For example, the disclosure provides microcin-MGE compositions formulated for specific uses, e.g., to treat, either therapeutically or prophylactically, bacterial infections, e.g., of the GI tract, or dysbiosis in a subject.

In another aspect, the disclosure features genetically engineered microorganisms that have a microcin operon and a controllable promoter for the microcin operon. In particular, the microcin operon has genes for the microcin production and the corresponding immunity peptide (mchB/mchI/mchX for MccH47 and mciA/mciI for MccI47) as well as mchA, mchC, mchD, mchE, and mchF genes, but lacks mchS1 or mchS4, or in general, any genes that encode enterobactin esterase and/or a enterochelin esterase homolog, which applicant discovered leads to significant reductions in growth rate. The controllable promoter controls a level of expression of the one or more microcin genes, thereby controlling the amount of microcin produced by the genetically engineered microorganism. Either or both of the microcin operon and the controllable promoter are heterologous to the microorganism.

As used herein, the term "microcin-MGE composition" includes microcin-MGE as the only modified form of microcin, but can also include unmodified microcin (microcin-u), such as Mcch47-u. The composition can also include pharmaceutically acceptable carriers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated herein by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
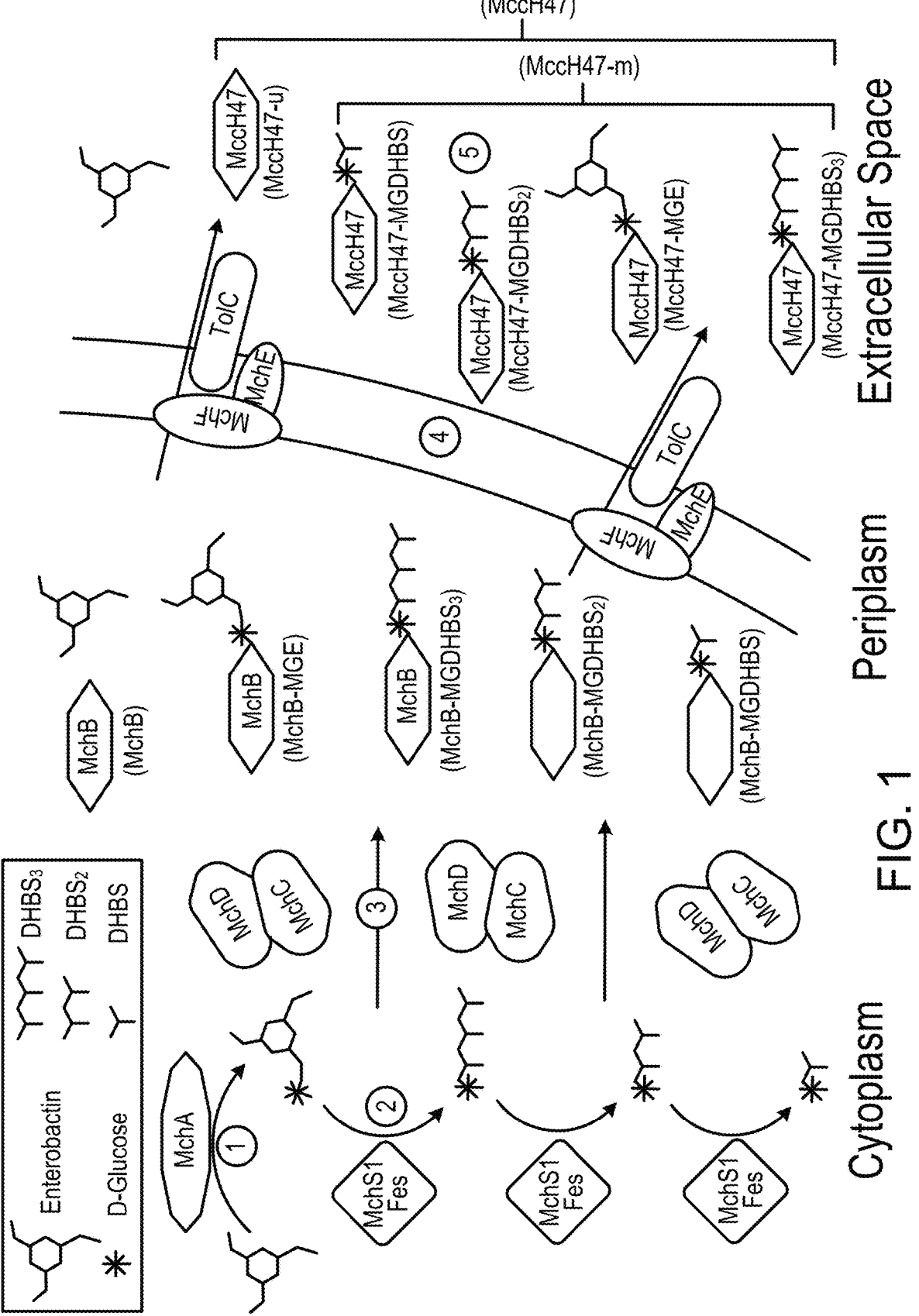
FIG. 1 is a schematic overview of MccH47's biosynthetic pathway:
(1) Enterobactin independently produced by the cell is glycosylated by MchA;
(2) MchS1/Fes (and IroD, not pictured) linearize enterobactin and remove individual subunits of DHBS;
(3) MGE/MGDHBS3/2/1 are coupled via ester linkage to the C-terminal serine residue of MchB, a process catalyzed by MchCD;
(4) MchB, with and without C-terminal post-translational modifications, is targeted for secretion by MchEF/TolC; and
(5) creating an extracellular environment containing the mixture collectively referred to as "MccH47." Only the MGE form is isolated and purified as described herein.

Members of drug-resistant bacteria, e.g., Enterobacteriaceae spp., including opportunistic pathogens (e.g., *Salmonella* spp.) are among the leading causes of morbidity and mortality worldwide. Overgrowth of these bacteria is considered a hallmark of intestinal dysbiosis. Some gut commensals produce microcins, small antimicrobial peptides that inhibit growth of select pathogens. As described herein, select gut commensals can be genetically altered and used to effectively treat pathogenic bacteria infections and/or to limit the growth of pathogenic bacteria.

Delivery of rationally-designed combinations of gastrointestinal commensals has the benefit of ensuring MDR/XDR pathogen decolonization via a number of concurring mechanisms including competition for nutrient and space, production of antimicrobial molecules and immune-system stimulation. However, the cost of large-scale production of these consortia linearly scales with the number of employed species (1-2 months per strain based on work from our industrial partners), thus making the generation of consortia of dozens of strains a big and time-consuming endeavor. Recent work has shown that addition of single strains of microcinogenic intestinal residents (i.e. bacteria capable of secreting small antimicrobial peptides) can lead to the killing of pathogenic Gram-negative Enterobacteriaceae, and therefore could be used as novel live biotherapeutics. However, because native microcin production is performed by strains with unknown mammalian gut colonization capability, and is dependent on the conditions experienced in the intestine (e.g., iron limitation), this phenomenon is difficult to control and thus exploit for therapies.

In our previous work, as described in PCT application WO 2019/055781, which is incorporated herein by reference, we have shown that heterologous overexpression of mature cathecol microcin H47 allows killing of *S. Typhimurium*, and based on this we developed the first proof-of-concept "sense-to-respond" genetically-engineered probiotic to kill *S. Typhimurium* through the heterologous production of microcin H47 after sensing tetrathionate, a signature of *S. Typhimurium*-induced intestinal inflammation[18].

Leveraging that work, we have built new prototypes of *E. coli* single-strain probiotics that produce a previously minimally-characterized microcin I47. Performing in vitro experiments using both heterologous I47 production from a probiotic or I47 for the first-time purified by us, we observed that microcin I47 is especially capable in killing CR *K. pneumoniae*, suggesting that we have identified a novel molecule for the killing of this deadly pathogen.

The present disclosure provides new purified Mcchh47-MGE and MccI47-MGE compositions and experiments to demonstrate the antimicrobial activity of MccH47-MGE against multiple clinically relevant MDR Enterobacteriaceae. MccH47 has minimum inhibitory concentrations measuring <75 µg/mL (<13 µM) for all strains of *E. coli, Salmonella, Shigella*, and *Proteus* tested, with no measurable activity against any non-Enterobacteriaceae strains tested.

The experiments disclosed in the examples below also show that MccH47-MGE has an inhibitory effect on MDR *K. pneumoniae* in solid media assays, yet no measurable MIC was achieved in liquid assays, suggesting that structure-based environments may play a role in microcin susceptibility.

Collectively, this disclosure establishes MccH47-MGE as an inhibitory form of modified MccH47 and demonstrates a straightforward pipeline that can be used for the design, overproduction, and purification of other class IIb microcins such as MccI47, MccE492, MccM, and MccG492. Moreover, the disclosure also demonstrates that MccH47-MGE can be used as a next generation antibiotic to achieve GI decolonization of MDR and XDR Enterobacteriaceae.

Microcins

Microcins are low-molecular-weight antimicrobial peptides secreted by members of the Enterobacteriaceae family. They include, e.g., Class I microcins, Class IIa microcins, Class IIb microcins, and Class IIc microcins. Class I microcins have molecular masses<5 kDa, are post-translationally modified, and bind to a spectrum of targets. Class IIb microcins are relatively large (~5-10 kDa) polypeptides and feature a C-terminal siderophore post-translational modification. Class IIb microcins include, e.g., Microcin H47 (MccH47), MccE492, MccM, MccG492, and MccI47.

MccH47

Microcin H47 (MccH47) is a bactericidal antibiotic. Due to its size, it shares with other microcins the ability to pass through cell membranes. MccH47 has been shown to be active to inhibit various bacteria, e.g., gram-negative bacteria, *E. coli, Salmonella, Enterobacter, Shigella, Klebsiella*, and *Proteus* spp. As described herein, the genes required for production of MccH47 are clustered in a 10-kb DNA segment located in the *E. coli* chromosome and include the genes: mchA, mchB, mchC, mchD, mchE, mchF, mchI, and mchX. Four genes, mchA, mchB, mchC, and mchD, are devoted to MccH47 synthesis; an immunity gene, mchI, encoding a small, 69-residue integral membrane peptide; and two further genes, mchE and mchF, are required for the secretion of the antibiotic into the extracellular medium.

A small gene, mchX, was found upstream of the immunity determinant; preliminary results point to its involvement in the activation of its own expression and probably in that of downstream immunity and production genes. The mchX, mchI, and mchB genes are located in the central region of the MccH47 genetic system, and are often referred as mchXIB. They are known to be transcribed in the same direction, towards mchB. Notably, the mchX gene may be involved in the activation of its own expression and the activation of downstream immunity and production genes.

MccH47 production is a process involving three main steps: synthesis of the precursor peptide MchB, subsequent maturation and post-translational modification of the molecule, and its final secretion. These MccH47 genes are described, e.g., in Vassiliadis et al. (2010),[14] which is incorporated herein by reference in its entirety. The complexity of the MccH47 antibiotic system parallels that of other microcin systems, such as those of microcins B17 and C7. MccH47 maturation, in which mchA, mchC, and mchD gene products are known to be necessary, is believed to endow the antibiotic molecule with the ability to enter cells.

mchA Gene Sequence:

(SEQ ID NO: 1)
ATGCGAAAACGTATTCTTTTTATTGGCCCACCGCTGTACGGTTTGTTATAC

CCATTGATTTCTCTGGCTCAGGCCTTTCGTGTAATCGGACATGATGTAGTA

ATTAGTAGTGCTGGCAAATTCGCGAATAAAGCAGCAGAAGCTGGACTGGT

-continued

```
TGTTTTTGATGCAGTTCCAGGTTTAGATTCAGAGGCTGGATATCGCCATCA

GGAAGAGTTGAGGAAAAAAAGTAATATTATTGGTCATTTCTCTTTTTTTAG

CGATGAAATGGCAGATAACCTCATCGATTTTGCAGGAAAATGGAGGCCAG

ATTTAATAGTCTATCCCCCGCTTGGTCCGGCAGGCCCATTGGTTGCTGCTA

AATATAGAATTCCTTCAGTGATGCTGGCTGTTGGATTCGCGCATACATCTG

CCCATATTCAGATGTTAAACCGTTCTTTAAGCAATGCTTACAGGCGGCATG

GAGTCAGCGGTCCACTATGTGATTTAGCATGGATTGATGTTGCTCCCCCAA

GTATGAGCATTCTTAAAAATGCTGAAGAACCGGTTATCTCAATGAGATAT

ATTCCTTATAACGGAGGTGCTGTAAAGGAAACATGGTGGGACAGGGATTC

TGATCGAAAACGTTTACTCATCAGCCTTGGCACTGTAAAACCAATGGTTG

ATGGTCTGGAGCTGATTTCATGGGTTATGGATTCTGCAAATGAAGTTGATG

CTGATATCATTTTGCAACTTGCAATAAATGCTCGTACTGGATTACGAAAAC

TACCATCAAATGTACGTCTGGTTGACTGGATACCTATGGGTGTATTCCTTA

ATGGAGCTGATGGATTTATTCATCATGGTGGCGCAGGTAATACCCTGACA

GCGTTGTATAGTGGGATACCACAGATTGTGTTTGGCGAAGGTGCAGATCG

CTCTGTTAATGCAGAAATTGTTGCGATGCGTGGGTGTGGGATTATTCCGGA

CAAGCATGGACTGACCAGTGATTTGGTAAATCGCCTGCTTTATGATGATTC

ACTACGCTTCTGTTCAGATCAGGTAGCCGCTGAAATGGCTGAACAACCCA

GTCCTGCAGAGATCGCAGAGGTTTTGATGAGAAAATTAAAAAACAACGG

GAAATAA.
``` mchC Gene Sequence:

```
                                        (SEQ ID NO: 2)
ATGAGTCATCAGTGTTCACTTTCTGAACTGAATGAAAACCTGGTGCCTTT

CACTGCCAGGCAGATCAAGTCCTCATTAATCTGGTGTGCAGAGGATGTCA

GAAATCCAGGCGAGCTGCAAAATGCCTGCAGTTATATTATCGATCCTGAC

AGTACGGCTTCTGCCAAAGTGTTCCATGCAGAGCGCTATGGTGGCAGTGG

TATTCAGCGTAATGGAGGTGGTGCACGTTGTGGGTTTGATGGTAACTACC

AGGTTAAAGGAATAGGAAGTAATCCGTTGGTTGGTGAAGGTACTGACGAA

CGTCATTCTAATGGTGCACTCGGCGCTGTTCATGCAATATATGAGGCTTT

GTGGGGAGAAGTACTGGCTCAAATATTACCTTATAGTGCTGTGCGGGTTC

GGGCGGTTTTACTTACAGATCTCTATACTGAAAAGGCATTTGAGCGCTCC

GGTATGAAATCACGAAGAGCCCTGTTGGTACGTGAGCCTGTTGTTCGCCC

GGCGCATTTTGAACGGGCACCATACTTCCAAGTAAAACCGGAGTATTCCA

GTCAGTTAATTCACGATGCCTGTCGGGTTAGATCTGTGATCCACAAGCTG

CCAGGATATCTACCTGTACCACCGGAAGAAATTGATGCTGAAGCACGAAC

TGATCCCCGGATTTATTGCATTGAGGGATTATGTGAACTGGCACGTCGTG

AGGCCTGGCAAATGGCATTTTGTCGAACACGTTTCCTGAGATTGACAACT

TCTCCTTCTAATATTGCAATGGATGGCAGATTAATGGATTTTAACGGACT

CAGTTGCTCGTTTCCGGGAGATTCCCCAGCTGATTTTGGGTATAAACTAA

GATTAGCTGAACTGGCAAAAGAACCGATGGTACTTATGCAAGGGCTGTCT
```

-continued

```
GATCTCTGCTTGTATATCGGAAAATATATGTTTGACCCTGACTTCACTCT

TGCAGCCCGTTTGAAGGTTGAGGAGATATTTCAGAAAACTTTTCATGAAG

CATGTTATTACTGTTATCTAGAACTGTTGGGTATTCCTGGAGAATTTATA

ACACAAAAAGAGATACCTGATATATTGAAACAACTGGTTAACAGTTTTGT

TGCATTACTCAATAAATACTGCGAGAAATCACATGCCCAAGATATTGTCA

ATCAGGATGGTTCACCATTGCAAAAGTTGGTTGTGACGCTAATCCATCAT

AGGCATAATCAAAAGCAGGCACTGAATAGTAGCATCAAGAATGATGTTTA

TTTCACCGTTGCACAACAGTGTTTTTCCCAGACTATCCACTGGCTGACGC

AAGGCAGTACCAGACGTCAGATAAATGCTTCATTACTCCTGAAAGAAATT

GAACATCATACCATGAAAAGGCTGCAACCCAGGGAAGAGCTGAGGAAAGA

GAATATGTGCGAAAAAATTGCCATCCTGCTGGATAATCATGGCGATGATC

CCCTTTTTTTACAAGAAGCAATTTCTGATATGAAAAATTTTATGCTTAAG

TTTTCCAGAGATGCATTTGGATATCTTGAACCGATAAGAAACACAGTGTA

A.
``` mchD Gene Sequence:

```
                                        (SEQ ID NO: 3)
ATGTCTTATATAAGGGAAACCATCAGAGGAAAAGATGAATGGACT

GTTTATGAACAGATAGGTTTTGCGGTCAGTTGTATGCTCTACAATCGTAAT

TACAGTCTGTATCCGGTGTTAACCATTCAATACTGGACTGAATATGCGATA

CAGCATAATCAGATTAAATTCCTGTTTGATTCACGAGGTTTTCCACTGGCG

TATATAACCTGGGCATATCTTGAGGCTGATACGGAAGCGCGCCTGCTCAG

GGATCCAGAATTCAGGTTGCATCCGTCTGAATGGAATGAAGATGGAAGGA

TCTGGATCCTGGATTTCTGTTGTAAACCAGGCTTTGGTCGAAAAGTTATTG

ACTATCTCATACAGCTTCAGCCATGGGGGGAAGGAGAAGTACGATGGTTA

AGCAGGCGAAAGAAAATTGTGACATACATCCCTGAGCGGCTGCATAAAA

CGTAG.
```

The mchB genes encodes the pre-Microcin H47 peptide. Once the peptide product of the mchB gene has gone through modification and secretion steps, the pre-Microcin H47 peptide becomes Microcin H47.

mchB Gene Sequence:

```
                                        (SEQ ID NO: 4)
ATGCGAGAAATAACAGAATCACAGTTAAGATATATTTCCGGGGCGGGAGG

TGCGCCAGCGACTTCAGCTAATGCCGCAGGTGCTGCAGCTATTGTTGGAG

CTCTCGCCGGAATACCTGGTGGTCCACTTGGGGTTGTAGTTGGAGCCGTA

TCTGCCGGTTTGACAACAGCAATTGGCTCGACCGTGGGAAGTGGTAGTGC

CAGTTCTTCTGCTGGTGGCGGTAGCTAA.
```

The mchE and mchF genes encode secretion proteins, which are necessary for MccH47secretion out of the cell.

mchE Gene Sequence:

(SEQ ID NO: 5)

TTGTTTCGTCAGGATGCTTTAGAAAACAGAAAAATGAAGTGGCAGGGACG

GGCAATATTACTTCCCGGAATACCACTATGGTTAATCATGCTGGGAAGCA

TTGTGTTTATTACGGCATTTCTGATGTTCATTATTGTTGGTACCTATAGC

CGCCGTGTTAATGTCAGTGGTGAGGTCACAACCTGGCCAAGAGCTGTCAA

TATATATTCAGGTGTACAGGGATTTGTTGTCAGGCAATTTGTTCATGAAG

GGCAGTTGATAAAAAAAGGGGATCCTGTTTATCTGATTGACATCAGTAAA

AGTACACGTAGTGGTATTGTCACTGATAATCATCGGCGGGATATAGAAAA

TCAGCTGGTTCGTGTGGACAACATTATTTCCCGTCTGGAAGAAAGTAAAA

AAATAACGTTAGATACCCTGGAAAAACAACGTCTGCAATACACAGATGCG

TTTCGTCGCTCATCAGATATTATACAGCGTGCAGAGGAAGGGATAAAAAT

AATGAAAAACAATATGGAGAATTACAGAAACTATCAGGCAAAAGGGCTGA

TTAATAAAGATCAGTTAACTAACCAGGTGGCATTATATTATCAGCAACAA

AACAATCTTCTCAGCCTGAGCGGACAGAACGAACAGAATGCCCTGCAGAT

AACCACTCTGGAGAGTCAGATTCAGACTCAGGCTGCAGATTTTGATAACC

GTATCTACCAGATGGAACTGCAACGGTACGAGTTACAGAAAGAACTGGTT

AACACTGATGTGGAGGGCGAAATTATTATCCGGGCGTTGACTGACGGGAA

AGTTGACTCCCTGAGTGTCACTGTCGGGCAAATGGTCAATACCGGAGACA

GCCTTCTGCAGGTTATTCCTGAGAACATTGAAAACTATTATCTTATTCTC

TGGGTCCCAAATGATGCTGTTCCTTATATTTCGGCTGGTGACAAAGTGAA

TATTCGTTATGAAGCCTTTCCGGCAGAAAAATTTGGGCAGTTCTCTGCTA

CGGTTAAAACTATATCCAGGACTCCTGCGTCAACACAGGAAATGTTGACC

TATAAGGGTGCACCACAGAATACGCCGGGCGCCTCTGTTCCCTGGTATAA

AGTCATTGCGATGCCTGAAAAGCAGATTATCAGATATGACGAAAAATACC

TCCCTCTGGAAAATGGAATGAAAGCCGAAAGTACACTATTTCTGGAAAAA

AGGCGTATTTACCAGTGGATGCTTTCTCCTTTCTATGACATGAAACACAG

TGCAACAGGACCGCTCAATGACTAA.

mchF Gene Sequence:

(SEQ ID NO: 6)

ATGACTAACGGGAGTTTCAGACAAATTATAAATCAGCTTGATATGC

GCTGGCGACGTCGTGTTCCGGTTATTCATCAGACGGAGACCGCTGAATGT

GGACTGGCCTGCCTGGCAATGATATGCGGTCATTTTGGTAAGAATATTGA

CCTGATATCTCTTCGCCGGAAGTTTAATCTCTCGGCCCGTGGAGCAAACCT

TGCAGGAATCAATGGAATAGCGGAGCAGCTGGGGATGGTCACCCGGGCT

CTTTCACTGGAGCTGGATGAACTTGGTGCCCTCAAAATGCCGTGTATTCTC

CACTGGGATTTCAGTCACTTTGTCGTGCTGGTCAGCGTAAAGCGTAACCGT

TATGTACTGCATGATCCGGCCAGAGGCAGAAGATATCTCGGTCGGGAGGA

AATGAGCCGGTATTTTACGGGCATTGCACTTGAGGTCTGGCCTGGAAGTG

AATTCCTGGCGGAAACCCAGCAGATCCGCATAAGTCTCCGTTCACTGATT

AACAGTATTTACGGTATTAAAAGAACACTGGCGAAAATTTTCTGTCTGTCA

GTTGTAATTGAAGCAATCAATCTGGTAATGCCGGTGGGGACTCAGCTGGT

TATGGATCATGCGATTCCGGCGGGGGACAGAGGGCTGCTGACGCTTATTT

CTGCTGGCCTGATGTTCTTTATATTGCTCAGGGCCGCGGTGAGTATGCTGC

GTGCATGGTCCTCACTGGTTATGAGCACGCTCATCAATATACAGTGGCAG

TCGGGTCTGTTTAACCATCTTCTCAGACTGCCGCTGGCGTTTTTTGAACGC

CGTAAATTAGGTGATATCCAGTCGCGTTTTGGCTCCCTTGACACTTTGAGG

GCCACCTTTACCACCTGTGTGGTTGGGGCAATCATGGACAGTATTATGGTT

GTGGGGGTTTTTGTGATGATGCTGTTATATGGAGGATATCTTACCTGGATA

GTGCTCGGTTTTACCATGGTTTACGTTCTTATTCGTCTGGTGACATACGGC

TATTACCGGCAAATATCGGAAGAAACTCTTGTCAGGGGGGCCCGGGCCAGC

TCCTATTTTATGGAAAGCCTGTATGGTATTGCCACGGTAAAAATCCAAGGT

ATGGCTGGGATCCGGGGAACACACTGGCTTAACCTGAAAATAGATGCGAT

CAATTCAGGTATTAAGTTAACCAAGATGGATTTGCTCTTCGGGGGGATAA

ATACTTTTGTTGCCGCCTGTGATCAGGTGGCGATTTTATGGCTGGGTGCAA

GCCTTGTGATCGATAATCAGATGACAATAGGGATGTTTGTGGCATTTGGTT

CTTTTCGTGGGCAGTTTTCGGATCGGGTTGCTTCGCTGACCAGTTTTCTTC

TTCAACTGAGAATAATGAGTCTGCATAATGAGCGCATTGCAGATATTGCAC

TACATGAAAAGGAAGAAAAGAAACCGGAAATTGAAATCGTTGCTGACAT

GAGCCCGGTTTCACTGGAAACCACTGATTTAAGCTACCGGTATGACAGCC

AGTCAGCACAGGTATTCAGTGGTCTGAATTTGTCTGTGGCTCCGGGAGAA

AGTGTGGCTATAACTGGTGCCTCCGGTGCCGGAAAAACCACATTAATGAA

AGTATTATGTGGACTGTTTGAACCAGATAGTGGAAAAGTACTGGTTAATG

GCACGGATATACGTCAACTTGGAATAAATAATTATCACCGTATGATAGCC

TGTGTTATGCAGGACGACCGGCTATTTTCAGGATCAATTCGTGAAAATATC

TGTGGGTTTGCAGAAGAAACAGACGACGAATGGATGACAGAATGTGCCA

GAGCAAGTCATATTCATGATGTGATAATGAAAATGCCAATGGGGTATGAA

ACGTTAATAGGTGAACTGGGGGAAGGTCTTTCCGGCGGTCAAAAACAGCG

TATATTCATTGCCCGAGCTTTATACCGGAAACCTGGAATATTATTTATGGA

TGAGGCTACAAGTTCTCTTGTGATACAGAAAGTGAACGTTTCGTGAATGCTG

CCATAAAAAAAATGAATATCACCCGGGTGATTATTGCACACAGAGAAACT

ACGTTGAGAACTGTTGACAGGATTATTTCTATTTAA.

The mchI gene encodes an immunity protein.

mchI Gene Sequence:

(SEQ ID NO: 7)

ATGAGTTATAAAAAACTGTACCAATTGACGGCTATATTTAGTTTACCTCT

TACTATCTTATTGGTTTCACTTTCATCCCTTCGGATTGTTGGCGAAGGGA

ATTCTTATGTTGACGTTTTTCTAAGCTTTATAATATTTCTTGGTTTTATT

GAGCTGATTCATGGGATTCGAAAGATTTTGGTCTGGTCAGGCTGGAAAAA

CGGAAGTTAA.

mchX Gene Sequence:

AAGTCGGCTTCCGGTATAGTAACACATGACTATGATGCCGATTATATTTG

TGGTTGTGGTGAAATTATGTGTCCTGGTTGCGGTCATGACCTATAA.

(SEQ ID NO: 8)
ATGGAATTTGCTACAAACAGGGTTACTGTAAATGACAGTCGGTCAG

CACTGTCATCAACTTTGCTGTTGTCTTTGATCATGAGCGCCACTCTACTG

GAATATTCTTTATCGATGACCTGA.

In some embodiments, the microcin that can be used in the compositions and methods as described herein is microcin J25. A detailed description regarding microcin J25 is described, e.g., in Bayro, Marvin J. et al. (2003). Structure of antibacterial peptide microcin J25: a 21-residue lariat protoknot. Journal of the American Chemical Society 125.41: 12382-1238, which is incorporated by reference herein in its entirety.

mchS1 Gene Sequence (This is a Gene that is Intentionally Omitted in the Genetically Engineered Vectors and Microorganisms Described Herein):

MccI47

Microcin I47 is a bactericidal antibiotic. Due to its size, it shares with other microcins the ability to pass through cell membranes. Microcin I47 has been reported to be produced by the MccH47 genetic system and detected in iron deprivation conditions (Azpiroz et al., 2011, PLOS ONE 6(10): e26179; Poey et al., 2006[16]).

(SEQ ID NO: 9)
ATGAAAAACTATCTTTTCCAGACTCCCGAAGATATTTGTGTACAGTTAAA

AAAAATGACACATCCTGTCACAATAAGAACAACAGATATTGCTAATTTCT

GGCACTATCTTGAGTCAGCAACTCTTCCGGTGATCACAAAAAGCACCACT

ACAGAAAATCGGGAGGTTACATTTCTGTGGCGCTCAGAGAAAGCAGTGCA

AGGCGTATATCTTCGCCTGAATCGTGTTACAGATAAAAAAGATGTCAAAA

AAGGACTAATGACTCATATCCCTTCGACAGATATCTGGATGCTGACACTG

GTGTTACCAGCTTCATATCGGGGCTCATACTCATTTATAGAAATTCCCAC

AGATATGACACAAAAGACATATTTCAACTAGGAAGTCGCTTCTCTCCAT

TACCCGGTAAATCTGATCCATTTAACAAAACAGCAGAAATAAATATACGA

GGATTCGGAGAATCAGTCCTTTCTCTTGATATGGCTCCTGAACAAAAGGA

ATGGGATGATACTTCCCATAAATGTACAGGTATTCTTTCAACATTACATT

CCTTTGTTGCAGGATATCAACGCCGGATTCGTTTATATTTTCCCCAGAAT

CCAACATCAGTACCTCTTGGATTACTTGTGTTACCTGATGCTGAAATATG

GTTTGACCGGATGGATATTACCCGGGCATTAGATATGGCCATTACCACTG

GTCATATTGCGCCAATGGCAATTATGGGGATAGACAATATTAATGAATCT

GATCGTATGAATATACTGGGAGGCAATAAAGAACTTATCTTTGATATAGC

GGAAAATCTGATACCCCAGTTATACAGAGACTACCCGAATATCGTATGGG

CTGGTCGTTCTAATACTATACTGGCCGGTCAGAGCCTCGGTGGAGTGACA

GCACTGATGGCAGCTATATATGCGTCGACAACATTTGGTACAATCATTAG

CCACTCACCTTCAATGTGGTGGAACCCTGACCAGGGCAGCCCGATTTTGT

TTACTGAGAATGATATCTCCTGGGTAAGTGAGCAGATACTTTCAGCGCCT

CCGAAAGATGTAAATATCCAACTTGGAGTCGGTTCTTTAGAAGGTACAAC

CGTCTCACATGTTCAGCGGTTGCATCAGTCGTTAATCGCAGCAGGTTTGG

AAAGTAACCTCACTGTCTATGCCGGTGGTCATGATTATGCCTGGTGGCGC

GGAGCAATTATTGATGCATTAGCAAATTATAATTGCAGGAAGATATCAGA

TAATAACTTTGTGTAA.

mchS4 Gene Sequence (This is a Gene that is Intentionally Omitted in the Genetically Engineered Vectors and Microorganisms Described Herein):

As disclosed herein, the genes required for production of MccI47 are clustered in a 10-kb DNA segment located in the E. coli chromosome and include the genes: mchA, mchC, mchD, mchE, mchF, mciA, and mciI. Four genes, mchA, mciA, mchC, and mchD, are devoted to MccI47 synthesis; an immunity gene, mciI, encoding a small, 144-residue peptide; and two further genes, mchE and mchF, are required for the secretion of the antibiotic into the extracellular medium.

MccI47 production is a process involving three main steps: synthesis of the precursor peptide MciA, subsequent maturation and post-translational modification of the molecule, and its final secretion. These genes are described, e.g., in Vassiliadis et al. (2010),[14] which is incorporated herein by reference in its entirety.

mchA Gene Sequence:

(SEQ ID NO: 1)
ATGCGAAAACGTATTCTTTTTATTGGCCCACCGCTGTACGGTTTGTTATA

CCCATTGATTTCTCTGGCTCAGGCCTTTCGTGTAATCGGACATGATGTAG

TAATTAGTAGTGCTGGCAAATTCGCGAATAAAGCAGCAGAAGCTGGACTG

GTTGTTTTTGATGCAGTTCCAGGTTTAGATTCAGAGGCTGGATATCGCCA

TCAGGAAGAGTTGAGGAAAAAAAGTAATATTATTGGTCATTTCTCTTTTT

TTAGCGATGAAATGGCAGATAACCTCATCGATTTTGCAGGAAAATGGAGG

CCAGATTTAATAGTCTATCCCCCGCTTGGTCCGGCAGGCCCATTGGTTGC

TGCTAAATATAGAATTCCTTCAGTGATGCTGGCTGTTGGATTCGCGCATA

CATCTGCCCATATTCAGATGTTAAACCGTTCTTTAAGCAATGCTTACAGG

CGGCATGGAGTCAGCGGTCCACTATGTGATTTAGCATGGATTGATGTTGC

TCCCCCAAGTATGAGCATTCTTAAAAATGCTGAAGAACCGGTTATCTCAA

TGAGATATATTCCTTATAACGGAGGTGCTGTAAAGGAAACATGGTGGGAC

AGGGATTCTGATCGAAACGTTTACTCATCAGCCTTGGCACTGTAAAACC

AATGGTTGATGGTCTGGAGCTGATTTCATGGGTTATGGATTCTGCAAATG

AAGTTGATGCTGATATCATTTTGCAACTTGCAATAAATGCTCGTACTGGA

TTACGAAAACTACCATCAAATGTACGTCTGGTTGACTGGATACCTATGGG

TGTATTCCTTAATGGAGCTGATGGATTTATTCATCATGGTGGCGCAGGTA (SEQ ID NO: 10)
ATGAATTGTGATAATAATCACAGAAATGAAGAATTCATTGTTACCTTTGA

TAAAGGCAACAAGCAAGACAATTCAAGACGAAAACACGATAATTTTCCTA

TAGAGGTAGAATCCTCCGTAGAGCTGGAGACACACTGTATCACAAATAAT

-continued

ATACCCTGACAGCGTTGTATAGTGGGATACCACAGATTGTGTTTGGCGAA

GGTGCAGATCGCTCTGTTAATGCAGAAATTGTTGCGATGCGTGGGTGTGG

GATTATTCCGGACAAGCATGGACTGACCAGTGATTTGGTAAATCGCCTGC

TTTATGATGATTCACTACGCTTCTGTTCAGATCAGGTAGCCGCTGAAATG

GCTGAACAACCCAGTCCTGCAGAGATCGCAGAGGTTTTGATGAGAAAATT

AAAAAACAACGGGAAATAA.

mchC Gene Sequence:

(SEQ ID NO: 2)

ATGAGTCATCAGTGTTCACTTTCTGAACTGAATGAAAACCTGGTGC

CTTTCACTGCCAGGCAGATCAAGTCCTCATTAATCTGGTGTGCAGAGGAT

GTCAGAAATCCAGGCGAGCTGCAAAATGCCTGCAGTTATATTATCGATCC

TGACAGTACGGCTTCTGCCAAAGTGTTCCATGCAGAGCGCTATGGTGGCA

GTGGTATTCAGCGTAATGGAGGTGGTGCACGTTGTGGGTTTGATGGTAAC

TACCAGGTTAAAGGAATAGGAAGTAATCCGTTGGTTGGTGAAGGTACTGA

CGAACGTCATTCTAATGGTGCACTCGGCGCTGTTCATGCAATATATGAGG

CTTTGTGGGGAGAAGTACTGGCTCAAATATTACCTTATAGTGCTGTGCGGG

TTCGGGCGGTTTTACTTACAGATCTCTATACTGAAAAGGCATTTGAGCGCT

CCGGTATGAAATCACGAAGAGCCCTGTTGGTACGTGAGCCTGTTGTTCGC

CCGGCGCATTTTGAACGGGCACCATACTTCCAAGTAAAACCGGAGTATTC

CAGTCAGTTAATTCACGATGCCTGTCGGGTTAGATCTGTGATCCACAAGCT

GCCAGGATATCTACCTGTACCACCGGAAGAAATTGATGCTGAAGCACGAA

CTGATCCCCGGATTTATTGCATTGAGGGATTATGTGAACTGGCACGTCGTG

AGGCCTGGCAAATGGCATTTTGTCGAACACGTTTCCTGAGATTGACAACTT

CTCCTTCTAATATTGCAATGGATGGCAGATTAATGGATTTTAACGGACTCA

GTTGCTCGTTTCCGGGAGATTCCCCAGCTGATTTTGGGTATAAACTAAGAT

TAGCTGAACTGGCAAAAGAACCGATGGTACTTATGCAAGGGCTGTCTGAT

CTCTGCTTGTATATCGGAAAATATATGTTTGACCCTGACTTCACTCTTGCA

GCCCGTTTGAAGGTTGAGGAGATATTTCAGAAAACTTTTCATGAAGCATG

TTATTACTGTTATCTAGAACTGTTGGGTATTCCTGGAGAATTTATAACACA

AAAAGAGATACCTGATATATTGAAACAACTGGTTAACAGTTTTGTTGCATT

ACTCAATAAATACTGCGAGAAATCACATGCCCAAGATATTGTCAATCAGG

ATGGTTCACCATTGCAAAAGTTGGTTGTGACGCTAATCCATCATAGGCAT

AATCAAAAGCAGGCACTGAATAGTAGCATCAAGAATGATGTTTATTTCAC

CGTTGCACAACAGTGTTTTTCCCAGACTATCCACTGGCTGACGCAAGGCA

GTACCAGACGTCAGATAAATGCTTCATTACTCCTGAAAGAAATTGAACAT

CATACCATGAAAAGGCTGCAACCCAGGGAAGAGCTGAGGAAAGAGAATA

TGTGCGAAAAAATTGCCATCCTGCTGGATAATCATGGCGATGATCCCCTTT

TTTTACAAGAAGCAATTTCTGATATGAAAAATTTTATGCTTAAGTTTTCCA

GAGATGCATTTGGATATCTTGAACCGATAAGAAACACAGTGTAA.

mchD Gene Sequence:

(SEQ ID NO: 3)

ATGTCTTATATAAGGGAAACCATCAGAGGAAAAGATGAATGGACT

GTTTATGAACAGATAGGTTTTGCGGTCAGTTGTATGCTCTACAATCGTAAT

TACAGTCTGTATCCGGTGTTAACCATTCAATACTGGACTGAATATGCGATA

CAGCATAATCAGATTAAATTCCTGTTTGATTCACGAGGTTTTCCACTGGCG

TATATAACCTGGGCATATCTTGAGGCTGATACGGAAGCGCGCCTGCTCAG

GGATCCAGAATTCAGGTTGCATCCGTCTGAATGGAATGAAGATGGAAGGA

TCTGGATCCTGGATTTCTGTTGTAAACCAGGCTTTGGTCGAAAAGTTATTG

ACTATCTCATACAGCTTCAGCCATGGGGGGAAGGAGAAGTACGATGGTTA

AGCAGGCGAAAGAAAATTGTGACATACATCCCTGAGCGGCTGCATAAAA

CGTAG.

The mchE and mchF genes encode secretion proteins, which are necessary for MccH47 secretion out of the cell. mchE Gene Sequence:

(SEQ ID NO: 5)

TTGTTTCGTCAGGATGCTTTAGAAAACAGAAAAATGAAGTGGCAGG

GACGGGCAATATTACTTCCCGGAATACCACTATGGTTAATCATGCTGGGA

AGCATTGTGTTTATTACGGCATTTCTGATGTTCATTATTGTTGGTACCTAT

AGCCGCCGTGTTAATGTCAGTGGTGAGGTCACAACCTGGCCAAGAGCTGTC

AATATATATTCAGGTGTACAGGGATTTGTTGTCAGGCAATTTGTTCATGAA

GGGCAGTTGATAAAAAAAGGGGATCCTGTTTATCTGATTGACATCAGTAA

AAGTACACGTAGTGGTATTGTCACTGATAATCATCGGCGGGATATAGAAA

ATCAGCTGGTTCGTGTGGACAACATTATTTCCCGTCTGGAAGAAAGTAAA

AAAATAACGTTAGATACCCTGGAAAAACAACGTCTGCAATACACAGATGC

GTTTCGTCGCTCATCAGATATTATACAGCGTGCAGAGGAAGGGATAAAAA

TAATGAAAAACAATATGGAGAATTACAGAAACTATCAGGCAAAAGGGCT

GATTAATAAAGATCAGTTAACTAACCAGGTGGCATTATATTATCAGCAAC

AAAACAATCTTCTCAGCCTGAGCGGACAGAACGAACAGAATGCCCTGCAG

ATAACCACTCTGGAGAGTCAGATTCAGACTCAGGCTGCAGATTTTGATAA

CCGTATCTACCAGATGGAACTGCAACGGTACGAGTTACAGAAAGAACTGG

TTAACACTGATGTGGAGGGCGAAATTATTATCCGGGCGTTGACTGACGGG

AAAGTTGACTCCCTGAGTGTCACTGTCGGGCAAATGGTCAATACCGGAGA

CAGCCTTCTGCAGGTTATTCCTGAGAACATTGAAAACTATTATCTTATTCT

CTGGGTCCCAAATGATGCTGTTCCTTATATTTCGGCTGGTGACAAAGTGAA

TATTCGTTATGAAGCCTTTCCGGCAGAAAAATTTGGGCAGTTCTCTGCTAC

GGTTAAAACTATATCCAGGACTCCTGCGTCAACACAGGAAATGTTGACCT

ATAAGGGTGCACCACAGAATACGCCGGGCGCCTCTGTTCCCTGGTATAAA

GTCATTGCGATGCCTGAAAAGCAGATTATCAGATATGACGAAAAATACCT

CCCTCTGGAAAATGGAATGAAAGCCGAAAGTACACTATTTCTGGAAAAAA

-continued

-continued

GGCGTATTTACCAGTGGATGCTTTCTCCTTTCTATGACATGAAACACAGTG

CAACAGGACCGCTCAATGACTAA.

mchF Gene Sequence:

(SEQ ID NO: 6)
ATGACTAACGGGAGTTTCAGACAAATTATAAATCAGCTTGATATGC

GCTGGCGACGTCGTGTTCCGGTTATTCATCAGACGGAGACCGCTGAATGT

GGACTGGCCTGCCTGGCAATGATATGCGGTCATTTTGGTAAGAATATTGA

CCTGATATCTCTTCGCCGGAAGTTTAATCTCTCGGCCCGTGGAGCAAACCT

TGCAGGAATCAATGGAATAGCGGAGCAGCTGGGGATGGTCACCCGGGCT

CTTTCACTGGAGCTGGATGAACTTGGTGCCCTCAAAATGCCGTGTATTCTC

CACTGGGATTTCAGTCACTTTGTCGTGCTGGTCAGCGTAAAGCGTAACCGT

TATGTACTGCATGATCCGGCCAGAGGCAGAAGATATCTCGGTCGGGAGGA

AATGAGCCGGTATTTTACGGGCATTGCACTTGAGGTCTGGCCTGGAAGTG

AATTCCTGGCGAAACCCAGCAGATCCGCATAAGTCTCCGTTCACTGATT

AACAGTATTTACGGTATTAAAAGAACACTGGCGAAAATTTTCTGTCTGTCA

GTTGTAATTGAAGCAATCAATCTGGTAATGCCGGTGGGGACTCAGCTGGT

TATGGATCATGCGATTCCGGCGGGGGACAGAGGGCTGCTGACGCTTATTT

CTGCTGGCCTGATGTTCTTTATATTGCTCAGGGCCGCGGTGAGTATGCTGC

GTGCATGGTCCTCACTGGTTATGAGCACGCTCATCAATATACAGTGGCAG

TCGGGTCTGTTTAACCATCTTCTCAGACTGCCGCTGGCGTTTTTTGAACGC

CGTAAATTAGGTGATATCCAGTCGCGTTTTGGCTCCCTTGACACTTTGAGG

GCCACCTTTACCACCTGTGTGGTTGGGGCAATCATGGACAGTATTATGGTT

GTGGGGGTTTTTGTGATGATGCTGTTATATGGAGGATATCTTACCTGGATA

GTGCTCGGTTTTACCATGGTTTACGTTCTTATTCGTCTGGTGACATACGGC

TATTACCGGCAAATATCGGAAGAAACTCTTGTCAGGGGGGCCCGGGCCAGC

TCCTATTTTATGGAAAGCCTGTATGGTATTGCCACGGTAAAAATCCAAGGT

ATGGCTGGGATCCGGGGAACACACTGGCTTAACCTGAAAATAGATGCGAT

CAATTCAGGTATTAAGTTAACCAAGATGGATTTGCTCTTCGGGGGGATAA

ATACTTTTGTTGCCGCCTGTGATCAGGTGGCGATTTTATGGCTGGGTGCAA

GCCTTGTGATCGATAATCAGATGACAATAGGGATGTTTGTGGCATTTGGTT

CTTTTCGTGGGCAGTTTTCGGATCGGGTTGCTTCGCTGACCAGTTTTCTTC

TTCAACTGAGAATAATGAGTCTGCATAATGAGCGCATTGCAGATATTGCAC

TACATGAAAGGAAGAAAGAAACCGGAAATTGAAATCGTTGCTGACAT

GAGCCCGGTTTCACTGGAAACCACTGATTTAAGCTACCGGTATGACAGCC

AGTCAGCACAGGTATTCAGTGGTCTGAATTTGTCTGTGGCTCCGGGAGAA

AGTGTGGCTATAACTGGTGCCTCCGGTGCCGGAAAAACCACATTAATGAA

AGTATTATGTGGACTGTTTGAACCAGATAGTGGAAAAGTACTGGTTAATG

GCACGGATATACGTCAACTTGGAATAAATAATTATCACCGTATGATAGCC

TGTGTTATGCAGGACGACCGGCTATTTTTCAGGATCAATTCGTGAAAATATC

TGTGGGTTTGCAGAAGAAACAGACGACGAATGGATGACAGAATGTGCCA

GAGCAAGTCATATTCATGATGTGATAATGAAAATGCCAATGGGGTATGAA

ACGTTAATAGGTGAACTGGGGGAAGGTCTTTCCGGCGGTCAAAAACAGCG

TATATTCATTGCCCGAGCTTTATACCGGAAACCTGGAATATTATTTATGGA

TGAGGCTACAAGTTCTCTTGATACAGAAAGTGAACGTTTCGTGAATGCTG

CCATAAAAAAAATGAATATCACCCGGGTGATTATTGCACACAGAGAAACT

ACGTTGAGAACTGTTGACAGGATTATTTCTATTTAA.

mchS1 Gene Sequence (This is the Gene that is Intentionally Omitted in the Genetically Engineered Vectors and Microorganisms Described Herein):

(SEQ ID NO: 9)
ATGAAAAACTATCTTTTCCAGACTCCCGAAGATATTTGTGTACAGT

TAAAAAAAATGACACATCCTGTCACAATAAGAACAACAGATATTGCTAAT

TTCTGGCACTATCTTGAGTCAGCAACTCTTCCGGTGATCACAAAAAGCACC

ACTACAGAAATCGGGAGGTTACATTTCTGTGGCGCTCAGAGAAAGCAGT

GCAAGGCGTATATCTTCGCCTGAATCGTGTTACAGATAAAAAAGATGTCA

AAAAAGGACTAATGACTCATATCCCTTCGACAGATATCTGGATGCTGACA

CTGGTGTTACCAGCTTCATATCGGGGCTCATACTCATTTATAGAAATTCCC

ACAGATATGACACAAAAGACATATTTCAACTAGGAAGTCGCTTCTCTCC

ATTACCCGGTAAATCTGATCCATTTAACAAAACAGCAGAAATAAATATAC

GAGGATTCGGAGAATCAGTCCTTTCTCTTGATATGGCTCCTGAACAAAAG

GAATGGGATGATACTTCCCATAAATGTACAGGTATTCTTTCAACATTACAT

TCCTTTGTTGCAGGATATCAACGCCGGATTCGTTTATATTTTCCCCAGAAT

CCAACATCAGTACCTCTTGGATTACTTGTGTTACCTGATGCTGAAATATGG

TTTGACCGGATGGATATTACCCGGGCATTAGATATGGCCATTACCACTGGT

CATATTGCGCCAATGGCAATTATGGGGATAGACAATATTAATGAATCTGA

TCGTATGAATATACTGGGAGGCAATAAAGAACTTATCTTTGATATAGCGG

AAAATCTGATACCCCAGTTATACAGAGACTACCCGAATATCGTATGGGCT

GGTCGTTCTAATACTATACTGGCCGGTCAGAGCCTCGGTGGAGTGACAGC

ACTGATGGCAGCTATATATGCGTCGACAACATTTGGTACAATCATTAGCC

ACTCACCTTCAATGTGGTGGAACCCTGACCAGGGCAGCCCGATTTTGTTTA

CTGAGAATGATATCTCCTGGGTAAGTGAGCAGATACTTTCAGCGCCTCCG

AAAGATGTAAATATCCAACTTGGAGTCGGTTCTTTAGAAGGTACAACCGT

CTCACATGTTCAGCGGTTGCATCAGTCGTTAATCGCAGCAGGTTTGGAAA

GTAACCTCACTGTCTATGCCGGTGGTCATGATTATGCCTGGTGGCGCGGA

GCAATTATTGATGCATTAGCAAATTATAATTGCAGGAAGATATCAGATAA

TAACTTTGTGTAA.

mchS4 Gene Sequence (Omitted):

(SEQ ID NO: 10)
ATGAATTGTGATAATAATCACAGAAATGAAGAATTCATTGTTACCT

TTGATAAAGGCAACAAGCAAGACAATTCAAGACGAAAACACGATAATTTT

-continued
CCTATAGAGGTAGAATCCTCCGTAGAGCTGGAGACACACTGTATCACAAA

TAATAAGTCGGCTTCCGGTATAGTAACACATGACTATGATGCCGATTATAT

TTGTGGTTGTGGTGAAATTATGTGTCCTGGTTGCGGTCATGACCTATAA.

The mciA gene encodes the pre-Microcin I47 peptide. Once the peptide product of the mciA gene has gone through modification and secretion steps, the pre-Microcin I47 peptide becomes Microcin I47.
mciA Gene Sequence:

(SEQ ID NO: 10)
ATGAGAGAAATATCAGATAACATGCTTGATTCCGTGAAAGGAGGG

ATGAATCTTAATGGATTACCTGCTTCTACTAATGTAATAGATCTACGTGGA

AAAGATATGGGAACATATATTGATGCTAATGGAGCATGCTGGGCTCCGGA

TACTCCATCCATCATCATGTATCCGGGGGGAAGTGGACCTTCTTATAGTAT

GAGTAGTTCCACATCCAGTGCAAACAGCGGCAGTTAA.

mciI Gene Sequence:

(SEQ ID NO: 11)
ATGTATCTTACGAAAAAGATTATAATAAGTATGATGTTTATATTAC

CATCTGCTGCATTTTCATCAGATCCACCTCCCCTTCAACAATCGTTAGAAA

AAACAACCTATTTTTCTATAGGTATGAATGGGTTTATAGGCTATCAGAGCG

AAGGGGAAAAATTATACACACACATTCTTACATTAGATAATCCCGAAGAG

ATATTTAAAAATATAATAAAAAATAGAAAGTCAACTAAGGAGTCTAAAAT

TTATGCTGCTTGTGGGCTATATTATTTAAACGTAGAAAATATAGAGTCATT

GTTTAATGAAAATGATAAACAAGAATATGTGTCTGTCTTAAGAGGGGATA

TTTTAACAAAAATAAAACTGAATGATATTCTGAATTCTGTGATAATAAATG

GTTGCAACACCAAATTAATATCTGAACATAAATGA.

In some embodiments, microcin I47 can be purified using an amylose resin column eluted with maltose. For example, cultures of *E. coli* producing microcin I47, e.g., *E. coli* NEB10β pHMT-I47, are grown under antibiotic selection (e.g., ampicillin and/or chloramphenicol), and in iron-limiting conditions, e.g., via the addition of 0.2 mM 2'2-dipyridyl, and induced, e.g., with isopropyl β-d-1-thiogalactopyranoside (IPTG). Cultures are grown for an additional time, e.g., 4 to 10 hours, e.g., 5 to 7 hours, post-induction, then pelleted and frozen overnight, e.g., at −20° C.

Cultures are then thawed in cold water, sonicated, and the crude lysate is passed through a resin column, e.g., an amylose resin (New England Biolabs, Ipswich, MA) column, to capture maltose-binding protein (MBP) fusion proteins, then finally eluted, e.g., with maltose. Elution is performed by adding the elution buffer (e.g., 200 mM NaCl, 20 mM Tris-HCl, 10 mM maltose; pH 7.5).

The eluent can be concentrated, for example, using Millipore Sigma (Burlington, MA) MWCO 10,000 filters. The concentrated MBP-MccI47 is then digested by an endopeptidase, such as the Tobacco etch virus nuclear-inclusion-a endopeptidase (TEV) (New England Biolabs, Ipswich, MA), yielding a buffered solution of MccI47, TEV, and MBP. This solution can then be further purified, e.g., by subsequent rounds of resuspension with Ni-NTA agarose resin (Qiagen, Hilden, DE). Ni-NTA slurry can be pelleted by centrifugation and the supernatant can be removed by pipetting.

Vectors

This disclosure provides various vectors comprising microcin genes and controllable promoters (e.g., inducible promoters). In some embodiments, the vector is a plasmid (e.g., pBR322, pLJV3, pJPMcH47, pttrMcH47, and pEX2000).

The vector can include genes for various microcins, e.g., Class I microcins, Class IIa microcins, Class IIb microcins, and/or Class IIc microcins. In some embodiments, the vector can include a set of genes for a Class IIa microcin (e.g., MccH47, MccE492, MccM, MccG492, and MccI47). In some embodiments, the vector can include a set of genes for MccH47 and/or microcin J25.

In some embodiments, the vector includes a set of genes for MccH47. These genes are required to express a functional MccH47 that can inhibit the growth of other bacteria. In some embodiments, the set of genes includes one, two, three, four, five, six, seven, or eight genes that are selected from the group consisting of mchA, mchB, mchC, mchD, mchE, mchF, mchX, mchI, mciA, and mcI. In some embodiments, the set of genes includes mchA, mchC, mchD, mchE, mchF; mchB, mchI, and mchX. In some embodiments, the set of genes includes mchA, mchC, mchD, mchE, mchF, mciA, and mciI.

In some embodiments, these genes can be located within one operon. Thus, in some embodiments, the operon includes one, two, three, four, five, six, seven, eight, or nine, or ten genes that are selected from the group consisting of mchA, mchB, mchC, mchD, mchE, mchF, mchX, mchI, mciA, and mchiI. In some embodiments, the operon contains mchC, mchD, mchE, mchF, mciA, and mciI. In some embodiments, the operon contains mchA.

In some embodiments, the set of genes or the operon is under the control of a controllable promoter. As used herein, the term "controllable promoter" refers to a promoter of which the initiation of transcription is controllable. For example, the initiation of transcription of a controllable promoter can be induced by a ligand, such as tetracycline, arabinose, galactose, isopropyl β-D-1-thiogalactopyranoside (IPTG), allolactose, etc. In some embodiments, the controllable promoter is rhaPBAD or Pttr.

High levels of microcins may be harmful to a subject, thus, according to the present disclosure, mechanisms can be introduced to the genetically engineered microorganisms to control the transcription of the genes or the operon, and thus control the level of microcins. The transcription of the microcin genes can be controlled by a controllable promoter. Some exemplary controllable promoters include, but are not limited to, Pttr promoter or pBAD promoter. The pBAD promoter is found in bacteria and was originally part of the arabinose operon that regulates transcription of araB, araA, and araD. Transcription initiation at the pBAD promoter occurs in the presence of high arabinose and low glucose concentrations. Upon arabinose binding to AraC, the N-terminal arm of AraC is released from its DNA binding domain via a "light switch" mechanism. This allows AraC to dimerize and bind the I1 and I2 operators. The AraC-arabinose dimer at this site contributes to activation of the pBAD promoter.

Additionally, cyclic AMP receptor protein (CAP) binds to two CAP binding sites upstream of the I1 and I2 operators and helps activate the pBAD promoter. In the presence of both high arabinose and high glucose concentrations however, low cAMP levels prevent CAP from activating the pBAD promoter. In the absence of arabinose, AraC dimerizes while bound to the O2 and I1 operator sites, looping the DNA. The looping prevents binding of CAP and RNA polymerase. Thus, without arabinose, the pBAD promoters are repressed by AraC. A detailed description of pBAD promoter can be found, e.g., in Schleif R. AraC protein, regulation of the L-arabinose operon in *Escherichia coli*, and the light switch mechanism of AraC action. FEMS Microbiol. Rev., (2010) 1-18, which is incorporated by reference in its entirety.
pBAD Promoter Sequence:

```
                                            (SEQ ID NO: 16)
CCACAATTCAGCAAATTGTGAACATCATCACGTTCATCTTTCCCTGGTTG
CCAATGGCCCATTTTCCTGTCAGTAACGAGAAGGTCGCGTATTCAGGCGC
TTTTTAGACTGGTCGTAATGAA.
```

In some embodiments, the controllable promoter is Pttr and is activated in the presence of tetrathionate as the inducing agent. The vector can also include genes that are required to determine the level of tetrathionate. Thus, the vector can include one, two, three, four or five genes that are selected from the group consisting of ttrA, ttrB, ttrC, ttrS, and ttrR. In some embodiments, the vector includes ttrS and ttrR.

In some embodiments, ttrA, ttrC, and ttrB are located within one operon. In some embodiments, this operon further includes mchB, mchC, mchD, mchE, mchF, mchX and mchI. In some embodiments, this operon is under the control of Pttr.

Figures 6A, 6B:
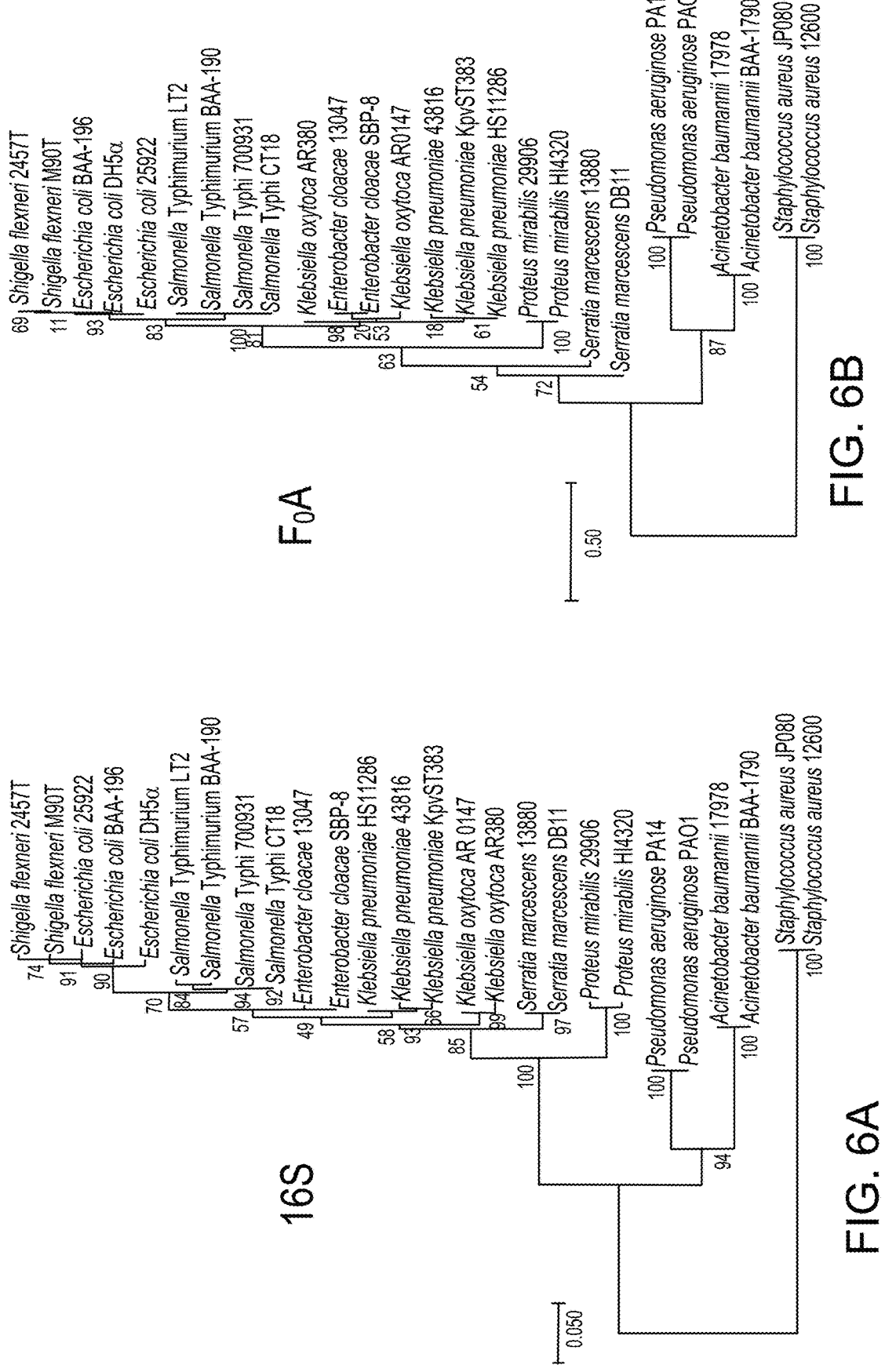
FIGS. 6A-6D are a set of phylogenetic trees that show yhylogenetic analysis of the 16S rRNA and the ATP synthase Fo subunits of the tested bacterial species. Phylogenetic positions are based on maximum likelihood and the following models with 100 Bootstrap replications each: (A) Kiramura-2 parameter model with gamma distribution, (B, C) Le and Gascuel model with gamma distribution and (D) Le and Gascuel model with uniform rates among sites. Bootstrap values are shown at the corresponding nodes. The branch-length indicator shows the frequency of substitutions per site. Bacterial genera or strains susceptible in MIC assay are colored in red, genera only susceptible in spot assay are colored in blue.
Figures 6C, 6D:
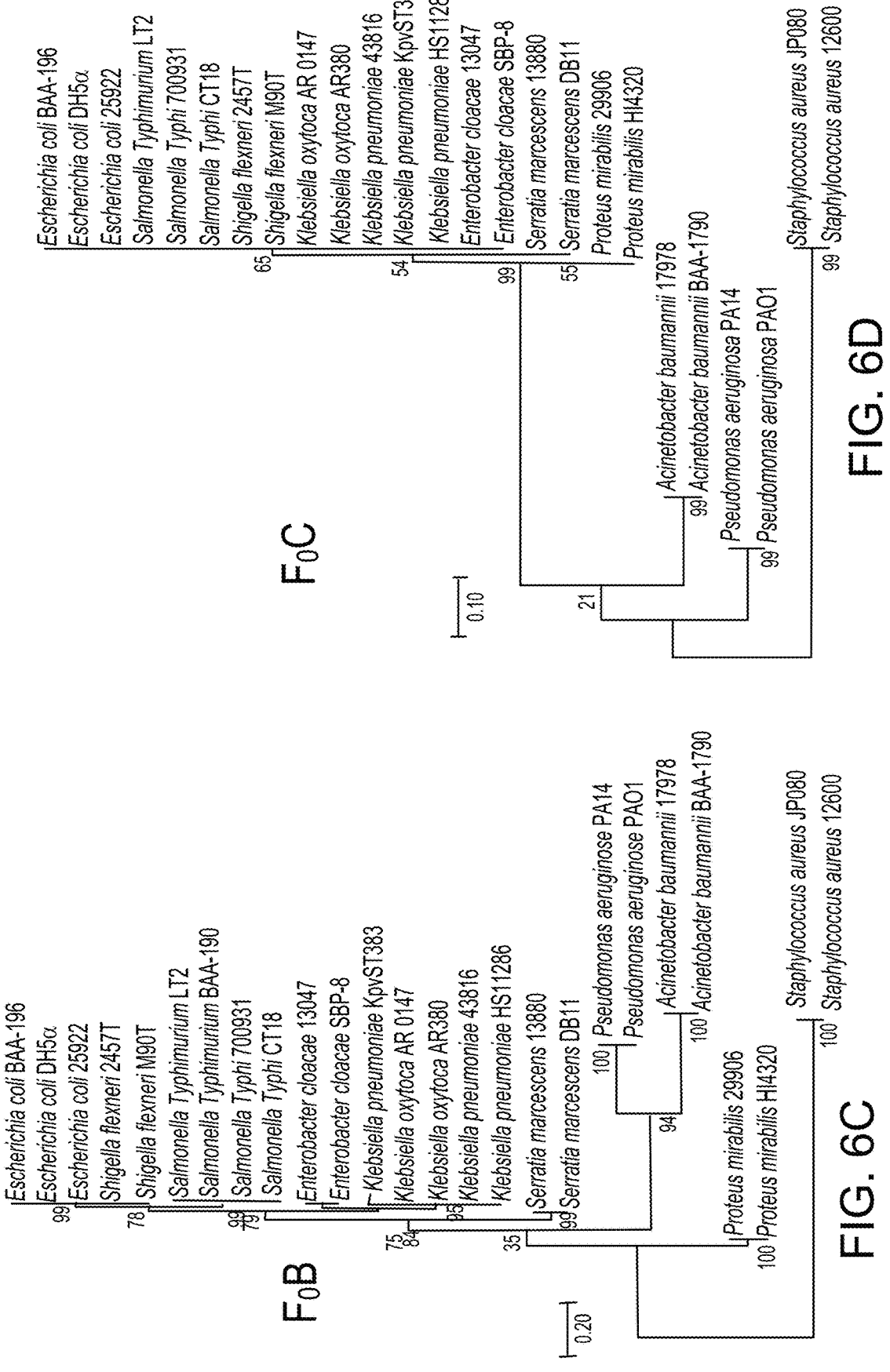

In some embodiments, the tetrathionate promoter (Pttr) is located immediately upstream of the mchXIB genes (mchX, mchI, mchB), and encoding them on a single transcript based on activation of the ttr promoter. The mchA can controlled by a constitutive promoter (e.g., J23119) (See e.g., FIG. 1B and FIG. 6A).
Pttr Promoter Sequence:

```
                                            (SEQ ID NO: 17)
CCCAATATCCCTGTCAATTATGTTGTTTTAGATCAACAACAAGCCGGGT

ATGTGGTTAACCACAATAGAGCGCACCCCGCCTCGATTTTTACACTGTA

AATCATCGACATTTTTTATTCATTACACATGAACCAACATCGTGACAAA

TGTTTCATTGTTGGCA.
```

J23110 Promoter Sequence:

```
                                            (SEQ ID NO: 18)
TTGACAGCTAGCTCAGTCCTAGGTATAATGCTAG.
```

This disclosure further provides genetically engineered microorganisms comprising the vectors as described herein. In some embodiments, the vector are integrated into the genome of the microorganism, e.g., by recombinant DNA techniques. Thus, in one aspect, this disclosure provides an engineered strain of EcN harboring a plasmid-based system carrying mchAXIBCDEF and ttrRSBCA, capable of producing MccH47 in response to environmental tetrathionate, resulting in the ability to inhibit and out-compete *Salmonella*.
Genetically Engineered Microorganisms Many microorganisms can be genetically engineered to treat bacterial infection as described herein. In some embodiments, a bacterium is used. In some embodiments, the bacterium is *E. coli* (e.g., *E. coli* Nissle 1917 or *E. coli* NGF-19). One useful *E. coli* strain is Nissle 1917 (EcN). *E. coli* Nissle 1917 is a Gram-negative species, which is easily cultured, easily genetically manipulated, able to colonize a human host, and easy to use for human probiotic applications. EcN is the active component of Mutaflor® (Ardeypharm GmbH, Herdecke, Germany), a microbial probiotic drug that is marketed and used in several countries. Clinical trials have shown EcN to be effective for maintaining remission of ulcerative colitis (UC), for stimulation of the of the immune system in premature infants, for treatment of infectious GI diseases, for the relief of constipation, and also for treatment of Irritable Bowel Syndrome in some patients.

In some embodiments, useful microorganisms that can be used in the methods disclosed herein include bacteria for making yogurt, e.g., *Lactobacillus delbrueckii* subsp. *bulgaricus* and *Streptococcus thermophiles*.

A vector or a set of genes as described herein can be introduced into a microorganism, e.g., a bacterium, such as, *E. coli*, to generate a genetically engineered microorganism by known molecular biology, microbiology, and recombinant DNA techniques. These techniques are familiar to one of skilled in the art and are explained fully in the literature. See, e.g., Molecular Cloning: A Laboratory Manual (Michael R. Green, Joseph Sambrook, Fourth Edition, 2012); Oligonucleotide Synthesis: Methods and Applications (Methods in Molecular Biology) (Piet Herdewijn, 2004); Nucleic Acid Hybridization (M. L. M. Andersen, 1999); Short Protocols in Molecular Biology (Ausubel et al., 1990), each of which is incorporated herein by reference in its entirety.

In some embodiments, the vector or the set of genes is integrated into the bacterial or other microbial genome.
Methods of Making New Purified MccH47-MGE and MccI47-MGE Compositions In general, and as described in past publications, MccH47, like other class IIb microcins, is actually a mixture of compounds. Biosynthesis of MccH47 begins with the gene product of mchB, a 75-residue protein with a 15-residue N-terminal leader peptide and a serine-rich C-terminus (SASSSAGGGS). The C-terminal serine residue of MchB can be post-translationally modified (PTM) with a C-monoglycosylated (MG) linear enterobactin or enterobactin derivative, a process catalyzed by the activity of MchCD.[14, 19,20] Enterobactin is a cyclic trimer of N-(2,3-dihydroxybenzoyl)serine (DHBS), and therefore intracellular MchB with a C-terminal PTM of MG trimer, dimer, or monomer of DHBS will be denoted as MchB-MGDHBS$_3$, MchB-MGDHBS$_2$, and MchB-MGDHBS, respectively. The C-glycosylation of enterobactin is catalyzed by a glycosyltransferase, commonly MchA and/or IroB in microcinogenic strains, resulting in MG enterobactin (MGE).[21,22] MGE production is followed by conversion to MGDHBS$_{3/2/1}$ by the enterobactin esterases MchS1, IroD and/or Fes, though conversion from enterobactin to DHBS$_{3/2/1}$ can occur prior to glycosylation.[21,23]

Export of MchB and the PTM MchB forms is mediated by TolC and MchEF, which comprise an ABC-transporter and secretion (AMS) or peptidase-containing ATP-binding transport (PCAT) system with a high degree of similarity to CvaAB of the microcin V system.[17] The N-terminal, 15-residue leader peptide of MchB is cleaved during export, resulting in a 60-amino acid protein, with or without C-terminal PTM, where the undefined mixture of such molecules will be collectively referred to as "MccH47". MccH47 lacking PTM (MccH47-u, where "-u" denotes the C-terminus is unmodified) is hypothesized to be unable to enter sensitive cells,[21] yet is still readily secreted and detectable in the supernatant of a producing strain, as has been demonstrated in EcN.[14]

FIG. 1 provides an overview of the proposed MccH47 biosynthetic pathway and associated nomenclature. As we have defined "MccH47" as the mixture of secreted MccH47 forms, with or without C-terminal PTM, and "MccH47-u" as secreted MccH47 without C-terminal PTM, we also propose to refer to the subset of MccH47 with C-terminal PTM as "MccH47-m," where "-m" denotes that the C-terminus is modified. Other important gene products of the mch cluster include MchI, for immunity, MchS4, which increases enterobactin production, and MchX, which is believed to regulate its own production and the production of other downstream mch genes.[21,24,25] However, only the microcin-MGE compositions, such as the MccH47 (and MccI47, and others)-MGE compositions or -siderophore compositions, shown in FIG. 1 are the new compositions of the present disclosure.

MccH47 is bactericidal, interacting with the $F_o$ region of ATP synthase, allowing unregulated influx of protons[26]. Uptake of MccH47-m is TonB-dependent, and mediated by the siderophore receptors Cir, Fiu, FepA, and IroN.[10,27] It is highly plausible, however, that any organism with sidero-phore receptors that can uptake enterobactin and/or its DHBS subunits is potentially susceptible to MccH47-m in iron limiting conditions. In fact, organisms as evolutionarily distant from E. coli as Pseudomonas aeruginosa have been demonstrated to import enterobactin conjugated with vari-able cargos (e.g., carboxylic acid) with relatively high promiscuity[28], implying that variability in susceptibility to MccH47-m among organisms capable of scavenging entero-bactin/DHBS may be mostly dependent on $F_o$ structure or some other feature not directly related to enterobactin/DHBS uptake.

Although MccH47 is a known antimicrobial peptide with respect to its biosynthesis, secretion, mode of uptake, and mechanistic target, the variability in production methods have led to notable deficiencies regarding spectrum of activity and potency. The present disclosure describes the new vector, e.g., plasmid, E. coli NEB10β pHMT-H47 (FIG. 2A), expressing a maltose binding protein (MBP)—MccH47 fusion, as well as a subset of genes from the mch cluster that were determined optimal for overexpression experiments (mchACDXIEFS4), based on previously published litera-ture.[12,21,24] The MBP-MccH47 fusion notably lacks the N-terminal leader peptide comprising the first fifteen amino acids of MchB.

The utilization of an MBP-fusion for purification of an antimicrobial peptide (AMP) from E. coli is a known approach[29,30] and we introduced a protease cleavage site, Tobacco etch virus (TEV) protease, between the MBP-MccH47 fusion to allow the release of MccH47 after MBP-mediated purification. Polyhistidine tags on MBP and TEV allowed for Nickel agarose-based removal of these contami-nants. Notably, the TEV recognition site utilized is 5'-EN-LYFQS-3', and TEV cleaves between the glutamine (Q) and serine (S), leaving an N-terminal serine as the first amino acid of the cleavage product, though this appeared to have a negligible impact regarding inhibitory activity.

In general, the microcin-MGE compositions are produced and purified by the following general steps:

1) omitting S1 (and S4);
2) growth in 6-12 L, under antibiotic selection (ampicillin and chloramphenicol), and under iron-limiting condi-tions to maximize enterobactin production, via the addition of 0.2 mM 2'-dipyridyl, and induced with 0.5 mM IPTG when cultures reached an optical density at 600 nm (OD600) of approximately 0.2;
3) growth for an additional 5-7 hours post-induction, then pelleted and frozen overnight at −20° C.;

4) thawing in cold water, sonicated, with crude lysate then was passed through an amylose resin (New England Biolabs, Ipswich, MA) column to capture the MBP fusion proteins, then finally eluted with maltose;
5) elution is performed by adding the elution buffer (200 mM NaCl, 20 mM Tris-HCl, 10 mM maltose; pH 7.5), discarding the first 5 mL (~8 mL amylose resin was used), and then capturing the next 30 mL of eluent;
6) concentration using Millipore Sigma (Burlington, MA) MWCO 10,000 filters, digestion by the addition of 10 μL of Tobacco etch virus nuclear-inclusion-a endopep-tidase (TEV) (New England Biolabs, Ipswich, MA), and incubation overnight at 4° C.;
7) the next day, the digestion is brought to room tempera-ture, an additional 5 μL of TEV was added, and allowed to incubate an additional 1-2 hours, yielding a buffered solution of MccH47, TEV, and MBP;
8) the solution is then further purified by subsequent rounds of resuspension with Ni-NTA agarose resin (Qiagen, Hilden, DE) (3-4 times), as both TEV and MBP contain 6× Histidine tags. Specifically, Ni-NTA agarose is resuspended and washed in elution buffer and added to the concentrated MBP+MccH47+TEV solution in a 1:2 volumetric ratio (i.e., 125 μL slurry to 25 μL digestion reaction); and
9) Ni-NTA slurry is pelleted by centrifugation, and the purified MccH47 in the supernatant is carefully removed by pipetting.

Cyclic, non-glycosylated enterobactin is the preferred substrate of Fes,[23] and therefore we hypothesize that the rapid glycosylation of cyclic enterobactin makes it imme-diately available for ester linkage to MccH47, making MccH47-MGE the only form of MccH47-m detectable in our experiments. Most interestingly, there appear to be no known instances of class IIb microcins which include a PTM of MGE, which serendipitously makes MccH47-MGE an entirely new form of MccH47. While our purified solution contains detectable levels of only MccH47-u and MccH47-MGE, because this remains a mixture of multiple MccH47 forms, we will continue to refer to this purified mixture as "MccH47."

In general, this is the first reported instance of a sidero-phore (e.g., MGE) being linked to an MBP fusion protein. Therefore, the present disclosure includes microcin-sidero-phore compositions that include, for example microcin-MGE, microsin-DHBS3, microcin-DHBS2, and microcin-DHBS1 when purified as described herein.

Methods of Treating Bacterial Infections

The purified MccH47-MGE and MccI47-MGE composi-tions disclosed herein have been shown to be active to inhibit various bacteria, e.g., gram-negative bacteria. In general, all class IIb microcin-MGE compositions can be used in a similar manner as described herein, as long as the microcin is meant for inhibiting various types of susceptible bacteria.

As used herein, the term "gram-negative bacterium" refers to a bacterium that do not retain the crystal violet stain used in the Gram staining method of bacterial differentia-tion. Gram-negative bacteria include, e.g., proteobacteria, cocci, bacilli, etc. The proteobacteria are a major group of gram-negative bacteria, including Escherichia coli (E. coli), Salmonella, Shigella, and other Enterobacteriaceae, Pseudomonas, Moraxella, Helicobacter, Stenotrophomonas, Bdellovibrio, acetic acid bacteria, Legionella etc. Gram-negative bacteria also include, e.g., the cyanobacteria, spi-rochaetes, green sulfur, and green non-sulfur bacteria. Medi-cally relevant gram-negative cocci include, e.g., Neisseria gonorrhoeae, Neisseria meningitidis, and Moraxella catarrhalis, Haemophilus influenzae. Medically relevant gram-negative bacilli include a multitude of species. Some of them cause primarily respiratory problems (Klebsiella pneumoniae, Legionella pneumophila, Pseudomonas aeruginosa), primarily urinary problems (Escherichia coli, Proteus mirabilis, Enterobacter cloacae, Serratia marcescens), and primarily gastrointestinal problems (Helicobacter pylori, Salmonella enteritidis, Salmonella typhi). Gram-negative bacteria associated with hospital-acquired infections include, e.g., Acinetobacter baumannii, which cause bacteremia, secondary meningitis, and ventilator-associated pneumonia in hospital intensive-care units.

In some embodiments, the composition and the methods as described herein can be used to treat gram-negative bacterial infection. In some embodiments, the bacterial infection is carbapenem-resistant enterobacteriaceae infection, Klebsiella oxytoca infection, Klebsiella pneumoniae infection, Campylobacter infection, extended spectrum enterobacteriaceae (e.g., E. coli, Salmonella, Shigella and Yersinia) infection.

The methods described in the present disclosure are effective for treating bacterial infection in a variety of subjects including humans and animals, such as laboratory animals, e.g., mice, rats, rabbits, or monkeys, or domesticated and farm animals, e.g., cats, dogs, goats, sheep, pigs, cows, horses, and other mammals, and birds, e.g., chickens and turkeys.

Healthcare providers can identify subjects in need of treatment for bacterial infection using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of bacterial infections and for treating bacterial infections. As used herein, the term "reducing the risk" refers to reducing the probability of developing a disorder or condition in a subject, who does not have, but is at risk of, or susceptible to, developing a disorder or condition.

In general, the new methods include administering the microcin-MGE compositions, e.g., MccH47-MGE and MccI47-MGE compositions, for example in lyophilized and/or powdered form, to a subject, e.g., orally, topically, and intravenously. In some embodiments, the microcin-MGE compositions, e.g., in lyophilized and/or powdered form, can be administered to a subject with some other known treatments for bacterial infection. For example, the microcin-MGE compositions, e.g., MccH47-MGE and MccI47-MGE compositions, can be used in combination with an antibiotic therapy, such as metronidazole, vancomycin, bacitracin, and/or teicoplatin.

In some embodiments, the microcin-MGE compositions are administered to the subject after the subject has received an antibiotic therapy. In some embodiments, the microcin-MGE compositions are administered to the subject before the subject has received an antibiotic therapy. In other embodiments, the microcin-MGE compositions are administered to the subject when the subject is under an antibiotic therapy.

In some embodiments, the microcin-MGE compositions can be administered to a subject with alkaline phosphatase and/or with (naturally) resistant probiotics to fill the ecological niches that are opened by the treatment with beneficial bacteria. These methods involve administering to the subject a composition including the microcin-MGE compositions and an amount of an alkaline phosphatase and/or probiotics effective to increase the number of commensal bacteria in the gastrointestinal tract, wherein alkaline phosphatase decreases the number of pathogenic bacteria in the gastrointestinal tract, or increases the number of commensal bacteria and decreases the number of pathogenic bacteria in the gastrointestinal tract, thereby modulating gastrointestinal tract flora levels in the subject. The alkaline phosphatase composition, and the methods of use is described in WO 2010/025267, which is incorporated by reference in its entirety.

Methods of Treating Dysbiosis

The compositions and the methods as described herein can be used to treat and/or reduce the risk of dysbiosis and its associated diseases.

Dysbiosis is a term for a microbial imbalance or maladaptation on or inside the body. As used herein, the term "intestinal dysbiosis" refers to microbial imbalance in intestines. Dysbiosis is most commonly reported as a condition in the gastrointestinal tract, particularly during small intestinal bacterial overgrowth (SIBO) or small intestinal fungal overgrowth (SIFO). It has been reported to be associated with various diseases, such as periodontal disease, inflammatory bowel disease, chronic fatigue syndrome, obesity, cancer, bacterial vaginosis, and colitis.

The methods described in the present disclosure are effective for treating dysbiosis in a variety of subjects including humans and animals, such as laboratory animals, e.g., mice, rats, rabbits, or monkeys, or domesticated and farm animals, e.g., cats, dogs, goats, sheep, pigs, cows, horses, and birds, e.g., chickens and turkeys.

Healthcare providers can identify subjects in need of treatment for dysbiosis using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of dysbiosis and for treating dysbiosis. As used herein, the term "reducing the risk" refers to reducing the probability of developing a disorder or condition in a subject, who does not have, but is at risk of, or susceptible to, developing a disorder or condition.

In some embodiments, the microcin-MGE compositions are administered to a subject, optionally with some other known treatments for dysbiosis.

Methods of Administration

The therapeutic methods disclosed herein (including prophylactic treatments) generally include administration of a therapeutically or prophylactically effective amount of the microcin-MGE compositions to a subject in need thereof. Such treatment will be suitably administered to subjects, particularly humans, suffering from, having, susceptible to, or at risk for a disease, disorder, or symptom of bacterial infection and/or dysbiosis. Determination of those subjects who are "at risk" can be made by any objective or subjective determination by a diagnostic test or opinion of a health care provider.

A subject is effectively treated when a clinically beneficial result ensues. This may mean, for example, a resolution of the symptoms associated with bacterial infection and/or dysbiosis, a decrease in the severity of the symptoms associated with bacterial infection and/or dysbiosis, or a slowing of the progression of symptoms associated with bacterial infection and/or dysbiosis.

The microcin-MGE compositions can also include a pharmaceutically acceptable carrier. The term "pharmaceutically acceptable" refers to molecular entities and compositions that do not produce an adverse, allergic or other untoward reaction when administered to a subject. The term "pharmaceutically acceptable carrier," as used herein, includes any and all solvents, e.g., purified water, dispersion media, coatings, antibacterial, isotonic and absorption delaying agents, buffers, excipients, binders, lubricants, gels, surfactants and the like, that may be used as media for a pharmaceutically acceptable substance.

The microcin-MGE compositions can be administered to a subject through many different routes, e.g., by endoscopy, by enteroscopy, by colonoscopy, by a nasoduodenal catheter, by enema, or by oral administration. In the case of oral administration, the microcin-MGE compositions can be delivered in a capsule or pill form. In some embodiments, the microcin-MGE composition is in a capsule form, e.g., packaged in gelatin capsules.

The present disclosure also provides a food composition comprising the microcin-MGE compositions. In some embodiments, the food composition comprises carbohydrates such as, but not limited to, starches such as are contained in rice flour, flour, tapioca flour, tapioca starch, and whole wheat flour, modified starches or mixtures thereof.

In some embodiments, the microcin-MGE compositions are in the form of a liquid, and thus can be used as a beverage. In some embodiments, the beverage composition comprising the microcin-MGE composition is naturally sweetened. Suitable natural sweeteners include, but are not limited to, sugars and sugar sources such as sucrose, lactose, glucose, fructose, maltose, galactose, corn syrup (including high fructose corn syrup), sugar alcohols, maltodextrins, high maltose corn syrup, starch, glycerin, brown sugar and mixtures thereof.

In some embodiments, the food or beverage compositions include milk or milk-derived product, e.g., yogurt. In some embodiments, a stabilizer may be combined with the milk-derived product. Combining a stabilizer with the milk-derived product may thicken the milk-derived product. In some embodiments, a stabilizer can be combined with the milk-derived product following completion of microorganism culture. The stabilizer can be selected from, as examples, gums, salts, emulsifiers, and their mixtures. Gums can be selected from, as examples, locust bean gum, xanthan gum, guar gum, gum arabic, and carageenan. In some embodiments, salts include, but are not limited to, sodium chloride and potassium chloride.

Dosage

The microcin-MGE compositions can be formulated in a unit dosage form, each dosage containing, for example, from about 0.005 mg to about 2000 mg of the microcin-MGE composition. The dosage scheduling can be approximately once per week, twice per week, three times per week, or four times per week. In some embodiments, the microcin-MGE compositions can be administered to a subject every day, every other day, every three days, every four days, every five days, every six days, or once per week. A person skilled in the art can refine the dosage scheduling as needed.

The phrase "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. When referring to these pre-formulation compositions as homogeneous, the active ingredient is typically dispersed evenly throughout the composition so that the composition can be readily subdivided into equally effective unit dosage forms.

The microcin-MGE compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the microcin-MGE composition.

Kits

The present disclosure also provides kits of the microcin-MGE compositions. In some embodiments, the kit includes a sterile container which contains a therapeutic or prophylactic composition including the microcin-MGE compositions. Such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit can also include instructions, e.g., information about the use of the microcin-MGE compositions for treating a bacterial infection. The kit can further contain precautions; warnings; indications; counter-indications; overdose information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The invention is further described in the following examples, which do not limit the scope of the invention described in the claims.

Example 1: Strains and Plasmids

Strains used in this study include *Escherichia coli* strain NEB10β (New England Biolabs, Ipswich, MA). All strains of Table 51 were purchased from ATCC (Manassas, VA).

Plasmid constructs developed in this work were transformed by electroporation into *E. coli* NEB10β cells. All media and additional reagents listed in this study were purchased from Sigma Aldrich, St. Louis, MO, unless otherwise indicated. Plasmids pHMT-H47 and pS4BAD-H47 were constructed using standard methods for Gibson Assembly[36], and the Gibson Assembly Master Mix (New England Biolabs, Ipswich, MA).

To construct pHMT-H47, seven fragments were amplified by polymerase chain reaction (PCR)[37] and assembled in a single Gibson Assembly reaction, prior to transformation of *E. coli* NEB10β. Fragments include: 1.) linearized pUC19, 2.) chloramphenicol resistance cassette from pTARA (Addgene #39491[38]), 3.) lacI and tac promoter from pMAL-c5X (New England Biolabs, Ipswich, MA), 4.) MBP, amplified using primers to add a 6×-Histidine N-terminal tag, from pMAL-c5X, 5.) mchB from pEX2000,[24] 6.) mchXI from pEX2000, 7.) mchCDEFAS4 from pPP2000, an unpublished vector developed previously by combining mchCDEF from pEX2000, mchA from pJPMcH47,[11] and mchS4 from pEX2000.

To construct pS4BAD-H47, three fragments were amplified by PCR and assembled via Gibson Assembly. Fragments include: 1.) linearized pUC19, 2.) araC and $P_{BAD}$ from pTARA (Addgene #39491[38]), 3.) mchXIBCDEFAS4 from pPP2000. DNA files for the plasmids constructed in this work have been uploaded in Zenodo at (DOI: 10.5281/zenodo.3483827) and can be opened with the free visualization software SnapGene Viewer (available online at snapgene.com/snapgene-viewer).

Example 2: Inhibition Assays

Solid media inhibition assays were carried out in a manner similar to those described in previous work.[11,31] First, single colonies of MccH47 producing strains were selected by pipette tip and stabbed into iron-limited LB agar supplemented with 0.2 mM 2,2'-dipyridyl, an iron-chelating agent, and 0.4% L-arabinose to induce MccH47 production. Colonies were incubated for ~36 hours to allow for extended production of MccH47 and inactivated by chloroform. Then 7.5 µL (approximately 4 µg) of the purified MccH47 solution was spotted, allowed to dry, and the plate was placed under ultraviolet light for 10 minutes. Target strains were then diluted 1:500 from an overnight culture in 3 mL LB with 0.2 mM 2,2'-dipyridyl, molten agar was added to a final concentration of 0.75%, and 3.5 mL of the inoculated soft agar medium was immediately overlaid and evenly spread on top of the MccH47 containing plate.

Figures 2A, 2B, 2C:
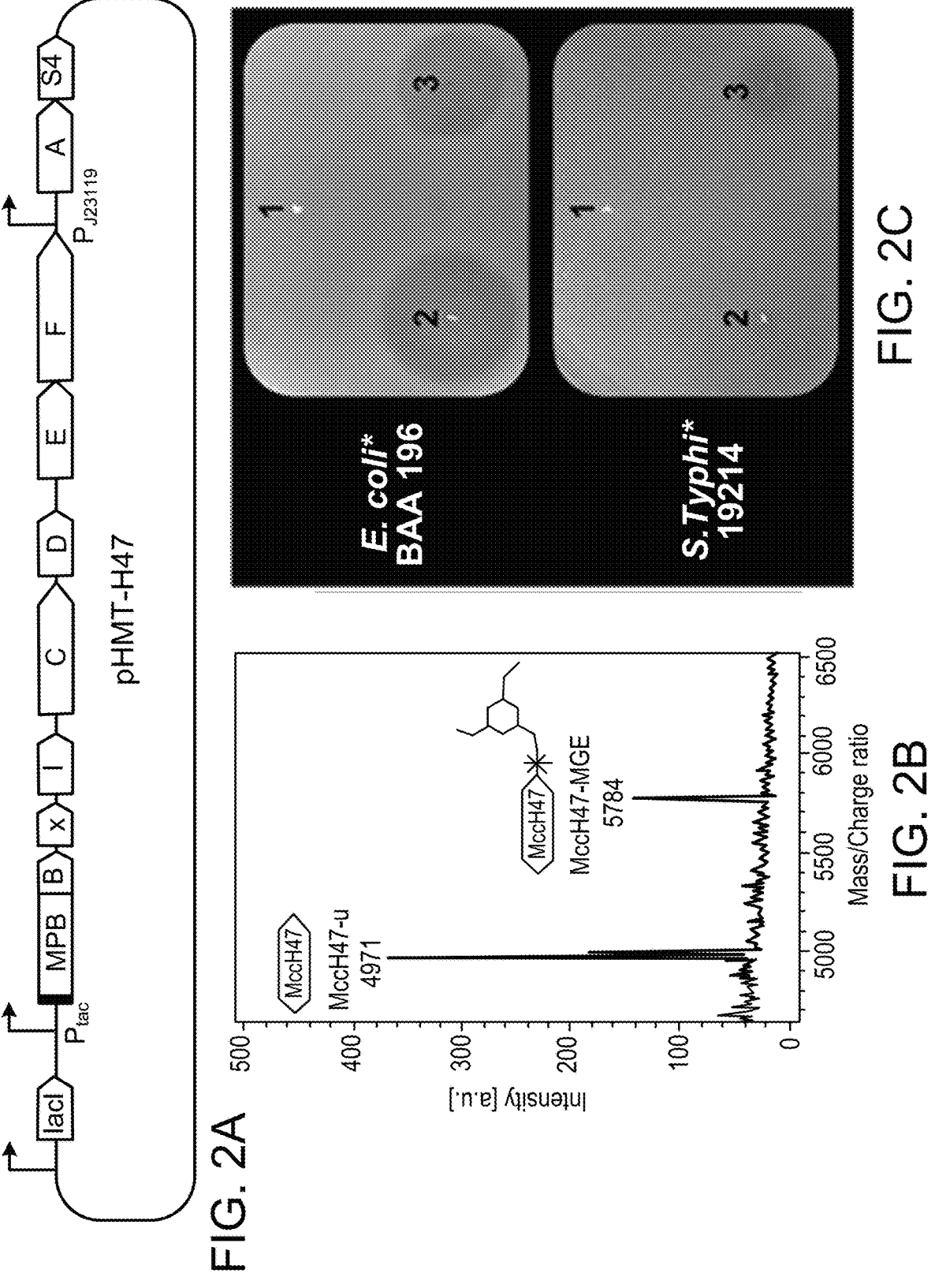
FIG. 2A is a schematic plasmid map of pHMT-H47, a pUC19-based plasmid that expresses a maltose binding protein (MBP)—MccH47-u fusion as well as the genes needed for post translational modification.
FIG. 2B is graph of MALDI-TOF analysis of purified MccH47 shows peaks for MccH47-u and MccH47-MGE, with a monoisotopic mass difference if 813 Da. Monoisotopic masses for each species are 4948 Da (MccH47-u) and 5761 (MccH47-MGE), each observed here with a 23 m/z increase corresponding to a sodium adduct. An additional peak immediately adjacent to the primary labelled MccH47-u peak is a disodiated adduct.
FIG. 2C is a representation of results of a static inhibition assay comparing MccH47 overproduction in stabs and after purification against an ESBL-producing *E. coli* (top) or an MDR *S. Typhi* strain (bottom). In this figure, (1) shows a stab of *E. coli* NEB10β harboring pUC19 (negative control), (2) shows a stab of *E. coli* NEB10β harboring pS4BAD-H47, and (3) shows a spot of ~4 μg of MccH47 purified from *E. coli* NEB10β harboring pHMT-H47.
Figure 7:
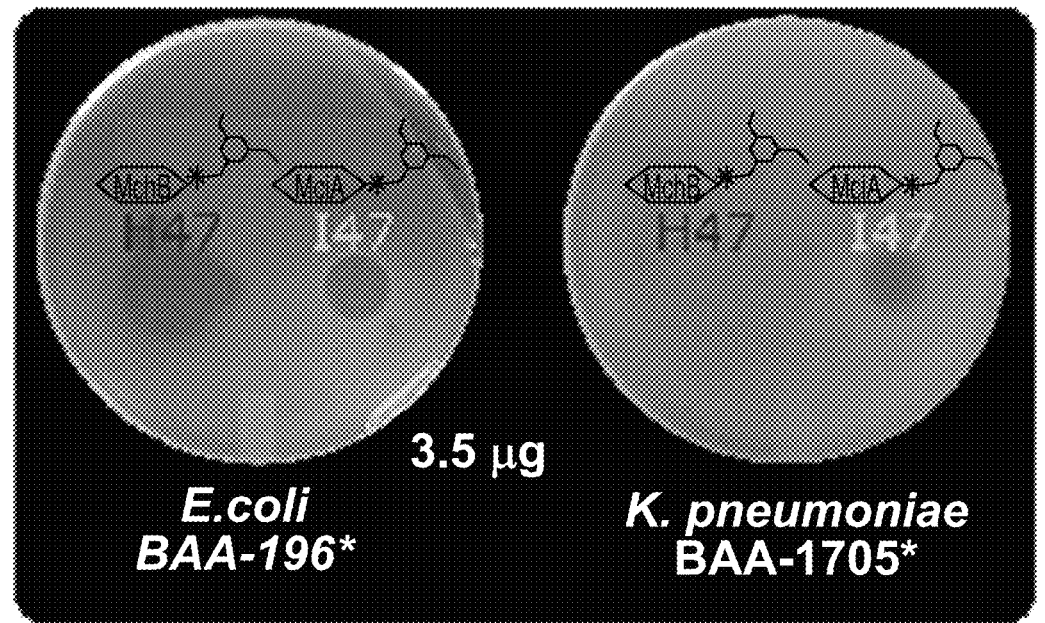
FIG. 7 shows the effect of purified MccI47-MGE compared to MccH47-MGE on killing MDR *E. coli* and *K. pneumoniae*.

As shown in FIG. 2B, 7.5 µL (~4.0 µg) of MccH47 were spotted onto LB agar plates, dried, and overlaid with the MDR *S. Typhi* strain 19214 (FIG. 2C). A clear zone of inhibition is visible in the *S. Typhi* lawn corresponding to the MccH47 solution, demonstrating the first example of a purified form of MccH47 inhibiting *Salmonella*. Additionally, a second plasmid (pS4BAD-H47), containing all of the same genes as pHMT-H47, except lacking MBP, was developed for the overexpression and secretion of MccH47 in live producing strains. It was stabbed into the agar medium, incubated for 36 hours and inactivated prior to the *S. Typhi* overlay, following previously established methods.[11,31]

An additional static inhibitory assay was performed in the same manner utilizing an extended spectrum beta-lactamase producing *E. coli* (ESBL-Ec) strain BAA-196, which clearly demonstrates the inhibitory capability of *E. coli* NEB10β pS4BAD-H47. Comparing the effect of purified MccH47 with the active form produced from a strain growing in an agar stab we clearly see a variable effect against the two targets. While ESBL-Ec is strongly inhibited by both, and perhaps more so by the stabbed culture, *S. Typhi* appears to be more strongly inhibited by the purified form.

Example 3: MccH47 Purification

The MBP-MccH47 was expressed and purified utilizing standard methods. Briefly, cultures of *E. coli* NEB10β pHMT-H47 were grown in 2 L LB broth, under antibiotic selection (ampicillin and chloramphenicol), and in iron-limiting conditions to maximize enterobactin production, via the addition of 0.2 mM 2'2-dipyridyl, and induced with 0.5 mM IPTG when cultures reached an optical density at 600 nm ($OD_{600}$) of approximately 0.2. Cultures were grown for an additional 5-7 hours post-induction, then pelleted and frozen overnight at −20° C. Cultures were then thawed in cold water, sonicated, and the crude lysate was passed through an amylose resin (New England Biolabs, Ipswich, MA) column to capture the MBP fusion proteins, then finally eluted with maltose.

Elution was performed by adding the elution buffer (200 mM NaCl, 20 mM Tris-HCl, 10 mM maltose; pH 7.5), discarding the first 5 mL (~8 mL amylose resin was used), and then capturing the next 30 mL of eluent. The eluent was then concentrated using MilliporeSigma (Burlington, MA) MWCO 10,000 filters. The concentrated MBP-MccH47 was then digested by the addition of 10 µL of Tobacco etch virus nuclear-inclusion-a endopeptidase (TEV) (New England Biolabs, Ipswich, MA), and incubated overnight at 4° C.

The following day, the digestion was brought to room temperature, an additional 5 µL of TEV was added, and the digestion was allowed to incubate an additional 1-2 hours, yielding a buffered solution of MccH47, TEV, and MBP. This solution was then further purified by subsequent rounds of resuspension with Ni-NTA agarose resin (Qiagen, Hilden, DE), as both TEV and MBP contained 6× Histidine tags. Specifically, Ni-NTA agarose was resuspended and washed in elution buffer and added to the concentrated MBP+ MccH47+TEV solution in a 1:2 volumetric ratio (i.e. 125 µL slurry to 250 µL digestion reaction). Ni-NTA slurry was pelleted by centrifugation, and the purified MccH47 in the supernatant was carefully removed by pipetting. This process was then repeated with fresh slurry and the final MccH47 solution was quantified via Qubit fluorometric quantitation.

Example 4: Minimum Inhibitory Concentration (MIC) Assays

MIC assays were performed by preparing two simple and robust media types: i.) 2× LB with 0.4 mM 2,2'-dipyridyl, and ii.) 1× LB, 0.2 mM 2,2'-dipyridyl, and 0.5× amylose resin elution buffer (200 mM NaCl, 20 mM Tris-HCl, 10 mM maltose; pH 7.5). The first well of each MIC assay was loaded with 20 µL of 2× LB; 0.4 mM 2,2'-dipyridyl, then with 20 µL of Ni-NTA purified amylose resin eluent, carrying the purified MccH47. This effectively rendered the first well with a media composition of 1× LB, 0.2 mM 2,2'-dipyridyl, 0.5× amylose resin elution buffer, containing the maximum MccH47 concentration for that particular MIC assay.

The remaining wells were loaded with 20 µL of the second media solution: 1× LB, 0.2 mM 2,2'-dipyridyl, and 0.5× amylose resin elution buffer, and then 2-fold serial dilutions were conducted eight times. Cultures of target strains were grown overnight in LB with shaking at 37° C. to stationary phase, then diluted 10,000-fold for inoculation into each well individually of the MIC assay. MIC assay plates were incubated at room temperature with gentle agitation and MIC's were determined as the lowest concentration as which no observable growth could be seen after 24 hours. All samples reported were done in at least triplicate, using at least three different MccH47 purifications. The median value of all assays was used as the reported MIC value.

Utilizing the ability to purify MccH47 (see FIG. 2B), we selected different representative members of Enterobacteriaceae for liquid MIC assays and included several MDR strains of clinical relevance; results are reported in Table 1, below, which shows test results for candidate members of *Klebsiella, Enterobacter, Staphylococcus, Acinetobacter,* and *Pseudomonas,* among others, but MIC exceeded 650 µg/mL (113 µM) in each case (see Table 2, below). In Table 1, * indicates multi-drug resistant, including carbapenemase-, extended spectrum beta-lactamase- and metallo-beta-lactamase-producers. In Table 2, bacterial strains susceptible in MIC assay are underlined, strains only susceptible in spot assay were all *Klebsiella pneumoniae,* and * indicates multi-drug resistant, including carbapenemase-, extended spectrum beta-lactamase-, and metallo-beta-lactamase-producers.

TABLE 1

Results of minimum inhibitory concentration (MIC) assays of purified MccH47 against multiple *Enterobacteriaceae* species

| Bacterial species | Strain | MIC (µg/ml) | MIC (µM) |
|---|---|---|---|
| *Escherichia coli* | 25922 | 30.8 | 5.3 |
| *Escherichia coli** | BAA-196 | 10.3 | 1.8 |
| *Escherichia coli* | DH5α | 6.3 | 1.1 |
| *Salmonella Typhimurium* | 19585 | 49.7 | 8.6 |
| *Salmonella Typhimurium* | 29630 | 36.6 | 6.3 |
| *Salmonella Typhimurium** | BAA-190 | 73.2 | 12.7 |
| *Salmonella Typhi** | 19214 | 61.5 | 10.6 |
| *Salmonella Typhi* | 700931 (TY2) | 52.3 | 9.0 |
| *Shigella flexneri* | 2457T | 14.0 | 2.4 |
| *Shigella flexneri* | M90T | 25.2 | 4.4 |
| *Proteus mirabilis* | 29906 | 30.8 | 5.3 |

TABLE 2

Strains of bacteria tested for susceptibility against MccH47-MGE.

| Bacterial Species | Strain | Origin |
|---|---|---|
| *Acinetobacter baumannii** | BAA-1790 | Human clinical isolate (sputum) |
| *Enterobacter cloacae** | BAA-2341 | Human clinical isolate |
| *Escherichia coli* | 25922 | Human clinical isolate |
| *Escherichia coli** | BAA-196 | Human clinical isolate |
| *Escherichia coli* | DH5α | Laboratory |
| *Klebsiella oxytoca** | 51983 | Human clinical isolate (blood) |
| *Klebsiella oxytoca* | 700324 | Human isolate (bioMérieux, Inc.) |
| *Klebsiella pneumoniae** | BAA-1705 | Human clinical isolate (urine) |
| *Klebsiella pneumoniae** | BAA-2146 | Human clinical isolate |
| *Klebsiella pneumoniae** | BAA-2342 | Human clinical isolate |
| *Klebsiella pneumoniae** | BAA-2524 | Human clinical isolate |
| *Proteus mirabilis* | 29906 | Human clinical isolate (urogenital) |
| *Pseudomonas aeruginosa* | PAM | Human clinical isolate |
| *Salmonella Typhimurium* | 19585 | Derived from LT2 (natural source) |
| *Salmonella Typhimurium* | 29630 | Derived from LT2 (natural source) |
| *Salmonella Typhimurium** | BAA-190 | Human clinical isolate |
| *Salmonella Typhi** | 19214 | Human isolate |
| *Salmonella Typhi* | 700931 | Derived from TY2 (Human isolate) |
| *Serratia marcescens* | DB11 | Derived from DB10 (*Drosophila*) |
| *Shigella flexneri* | 2457T | Human clinical isolate |
| *Shigella flexneri* | M90T | Human clinical isolate |
| *Staphylococcus aureus* | 27661 | Human isolate |

MccH47 activity demonstrated strong effects against all members of *E. coli, Shigella,* and *Salmonella* strains tested at concentrations lower than 75 µg/mL (13 µM) with no considerable difference between antibiotic-sensitive and MDR strains. Note that the reported MIC values are rather conservative due to the purification and the inclusion of MccH47-u, yet when comparing on a molar basis (Table 1), MccH47 potency is of the same magnitude as commonly used antibiotics.[32]

No MIC was achieved against strains of *K. pneumoniae, K. oxytoca, Acinetobacter baumannii, P. aeruginosa, Staphylococcus aureus, Serratia marcescens,* or *Enterobacter cloacae,* even at concentrations as high as 650 µg/ml (113 µM).

Even though *A. baumanii* and *P. aeruginosa* are known siderophore scavengers, with the latter known to take up enterobactin linked to a wide variety of R-group cargos[28,34], no alteration of growth pattern was observed in liquid MIC assays.

These results suggest that target affinity to ATP synthase is not the only factor determining MccH47-MGE susceptibility but other mechanisms, such as import through siderophore receptors, may be involved. It is noteworthy that the MIC values reported here correspond to inhibition by the MccH47-MGE and MccH47-u mixture and that these values may vary if utilizing a different form or mixture of MccH47, as target organisms with variable siderophore receptor expression may import each variant at a different rate.

Regarding the capability of microcin-MGE compositions like MccH47-MGE compositions to be used as a new class of antibiotics, there are few points to consider. First, rather than systemic application of intravenous antibiotics, or oral delivery of compounds intended for diffusion into the bloodstream, AMP's are proteins to be delivered to the point of infection—the mammalian gut. The present disclosure demonstrates the antimicrobial activity of microcin-MGE compositions, such as MccH47-MGE compositions, against multiple clinically relevant MDR Enterobacteriaceae. Additionally, we provide the first demonstration of a MBP-protein fusion to undergo post-translational covalent attachment to a glycosylated siderophore, here MGE, in the *E. coli* host, and we used this methodology to purify the novel MccH47-MGE composition.

The purified MccH47-MGE compositions tested as described herein have minimum inhibitory concentrations measuring <75 µg/mL (<13 µM) for all strains of *E. coli, Salmonella, Shigella,* and *Proteus* tested, with no measurable activity against any non-Enterobacteriaceae strains tested. We also show that the purified MccH47-MGE compositions have an inhibitory effect on MDR *K. pneumoniae* in solid media assays, yet no measurable MIC was achieved in liquid assays, suggesting that structure-based environments may play a role in microcin susceptibility. Collectively, this disclosure establishes MccH47-MGE compositions as an inhibitory form of MccH47-m and demonstrates a straightforward pipeline for the design, overproduction, and purification of other uncharacterized class IIb microcins such as MccI47, MccE492, MccM, and MccG492. Moreover, this disclosure supports the use of MccH47-MGE compositions as a viable therapeutic composition for use as a next generation antibiotic to achieve GI decolonization of MDR and XDR Enterobacteriaceae.

To test the activity of MccI47-MGE, we purified MccI47-MGE and selected different representative members of *Enterobacter, Escherichia, Klebsiella, Proteus, Salmonella, Serratia, Shigella,* and *Staphylococcus* for liquid MIC assays and included several MDR strains of clinical relevance. Table 3 below shows test results for candidate members. In Table 3, results are displayed as the average of three biological replicates. * indicates multi-drug resistant strain.

Mccl47 activity demonstrated strong effects against all members of *E. coli, Shigella, Klebsiella, Salmonella* and *Shigella* strains tested at concentrations lower than 40 µg/mL (6.4 µM) with no considerable difference between antibiotic-sensitive and MDR strains.

were prepared as follows: 15 mg/mL 2,5-dihydroxybenzoic acid in methanol, ~10 mg/mL alpha-cyano-4-hydroxycin- namic acid in 70% acetonitrile, 0.1% trifluoroacetic acid in water. 5 µL of 0.5 mg/mL POI solution in water was mixed with 5 µl of each matrix solution and after brief vortexing 1 µL of the mixture was spotted on the MALDI target and allowed to dry at room temperature. Spectra were obtained

TABLE 3

Results of Minimum Inhibitory Concentration (MIC) assays displaying the effect of Mccl47-MGE on a set of target bacteria

| Bacterial species | Strain | Origin | MIC (µg/ml) | MIC (µM) |
|---|---|---|---|---|
| *Enterobacter cloacae** | BAA-2341 | Human clinical isolate | 107.25 | 17.1 |
| *Escherichia coli* | 25922 | Human clinical isolate | 1.58 | 0.3 |
| *Escherichia coli** | BAA-196 | Human clinical isolate | 4.43 | 0.71 |
| *Escherichia coli* | DH5α | Laboratory | 2.26 | 0.4 |
| *Klebsiella pneumoniae** | BAA-1705 | Human clinical isolate (urine) | 36.13 | 5.8 |
| *Klebsiella pneumoniae** | BAA-2146 | Human clinical isolate | 29.44 | 4.7 |
| *Klebsiella pneumoniae** | BAA-2342 | Human clinical isolate | 16.39 | 2.6 |
| *Klebsiella pneumoniae** | BAA-2524 | Human clinical isolate | 14.72 | 2.3 |
| *Proteus mirabilis* | 29906 | Human clinical isolate (urogenital) | >197.25 | >31.5 |
| *Salmonella Typhimurium* | 19585 | Derived from LT2 (natural source) | 7.96 | 1.3 |
| *Salmonella Typhimurium* | 29630 | Derived from LT2 (natural source) | 6.31 | 1.0 |
| *Salmonella Typhimurium** | BAA-190 | Human clinical isolate | 12.63 | 2.0 |
| *Serratia marcescens* | DB11 | Derived from DB10 (*Drosophila*) | 107.00 | 17.1 |
| *Shigella flexneri* | 2457T | Human clinical isolate | 0.42 | 0.1 |
| *Shigella flexneri* | M90T | Human clinical isolate | 0.42 | 0.1 |
| *Staphylococcus aureus* | 27661 | Human isolate | >197.25 | >31.5 |

Figure 5:
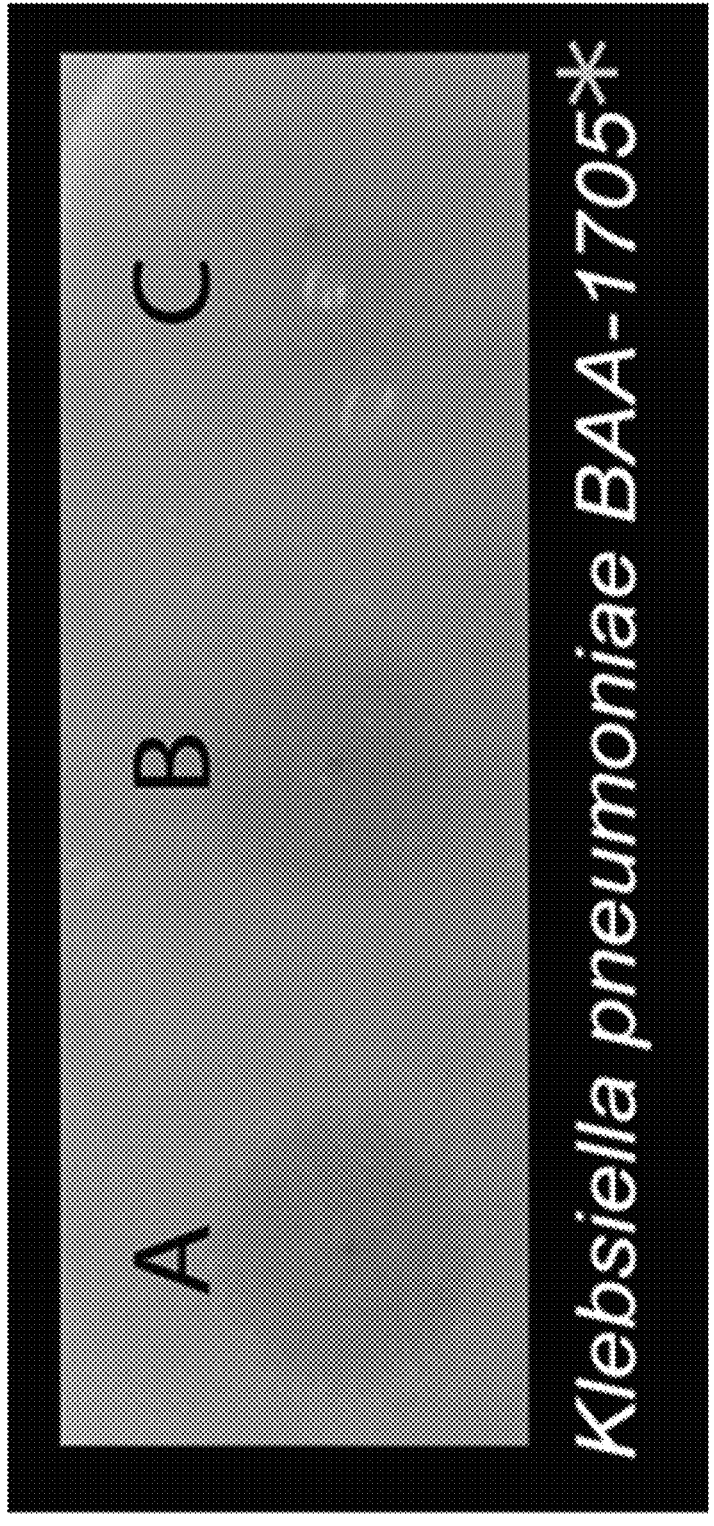
FIG. 5 is representation of static inhibitory assay utilizing serial dilutions of MccH47 against *K. pneumoniae*. MccH47 solution isolated from *E. coli* NEB10β harboring pHMT-H47 was spotted in 25 μL aliquots as 2-fold serial dilutions starting at A=7.03 μg. Once dried, the plate was overlaid with *K. pneumoniae* strain BAA-1705 soft agar. Inhibitory halos were clearly observable in spots A and B, corresponding to spots of 7.03 μg and 3.51 μg, respectively. Spot C (1.75 μg) demonstrates a faint halo of inhibition and represents the last observable halo.

In liquid MIC assays, some minor growth retardation was observable for *K. oxytoca* and *K. pneumoniae* isolates, which led us to speculate that inhibitory assays on solid media may more clearly demonstrate inhibitory activity. Spatially-structured environments have been shown to impact bacterial toxin activity[33], and indeed, halos of inhi- bition were observable against *K. pneumoniae* in aliquots containing as low as 1.75 µg MccH47 (FIG. 5).

We further compared the effects of purified Mccl47-MGE and purified MccH47-MGE on killing MDR *E. coli* (BAA- 196) and *K. pneumoniae* (BAA-1705) strains. As shown in FIG. 7, halos of inhibition were observable against *E. coli* (BAA-196) and *K. pneumoniae* (BAA-1705) in aliquots containing as low as 3.5 µg Mccl47-MGE. Halo of inhibi- tion was observable against *E. coli* (BAA-196) in aliquot containing as low as 3.5 µg MccH47-MGE.

These results demonstrate that Mccl47-MGE and MccH47-MGE compositions are viable therapeutic compo- sitions for use as a next generation antibiotics.

Example 5: Mass Spectrometry

For MccH47 to be analyzed via Mass spectrometry, samples were purified, as described above, except that buffer replacement with deionized water (pH=8.0) in MWCO 10,000 filters was immediately conducted after the initial MWCO 10,000 filter step. TEV digestion and Ni-NTA resin purification were performed in deionized water (pH=8.0), and the resulting solution was processed at the Mass Spec- trometry Core Facility at the University of Massachusetts Amherst. Mass spectra were acquired using a Bruker ultra- fleXtreme MALDI-TOF mass spectrometer. A mixed matrix approach was found to yield the best overall signal. Matrices using reflectron positive ion mode using sufficient laser fluency and shot number to obtain an acceptable signal:noise ratio.

Figure 3:
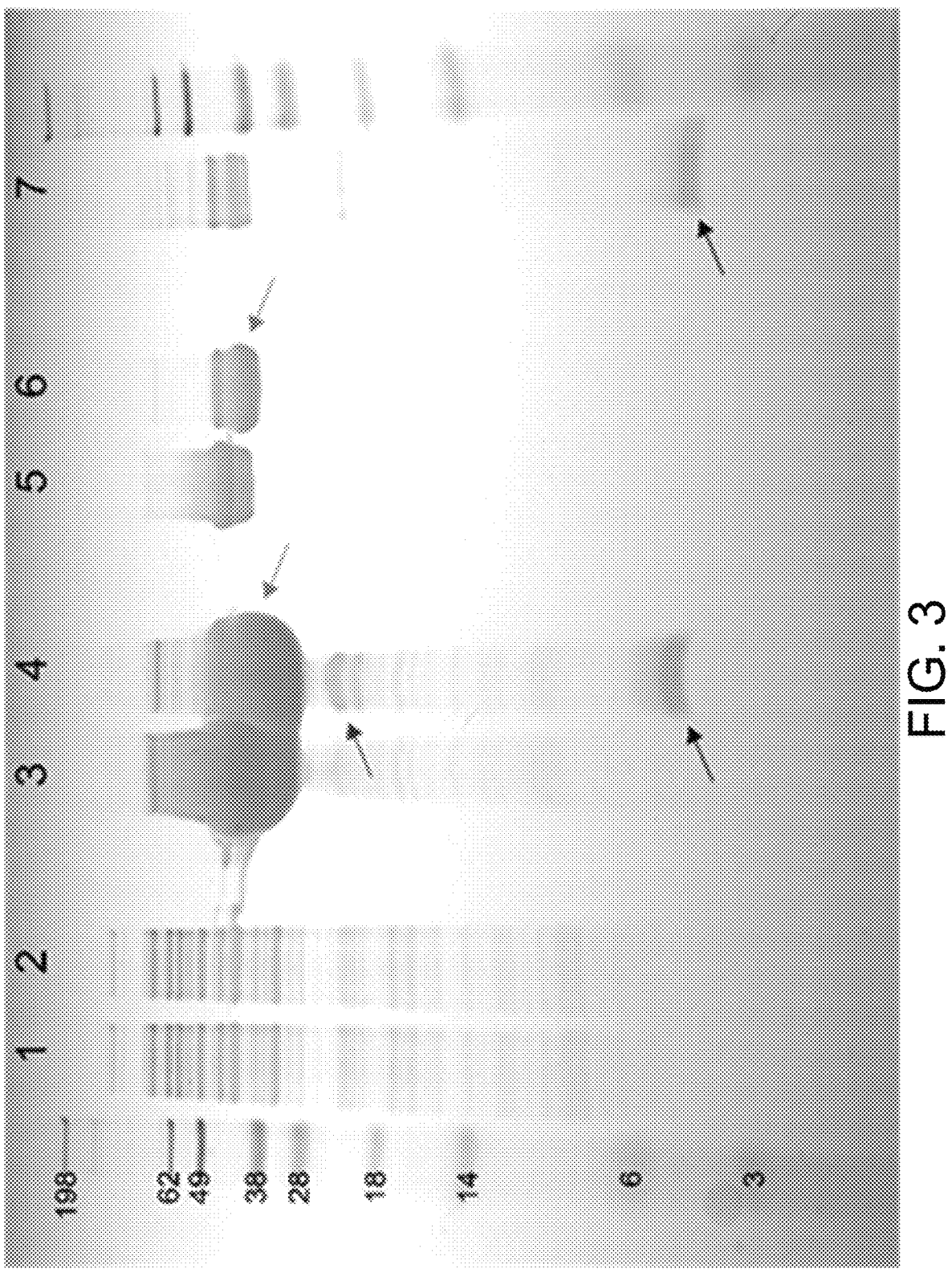
FIG. 3 is representation of a polyacrylamide gel electrophoresis result from overproduction of *E. coli* NEB10β pHMT-H47 and purification of MccH47. Far left and right: SeeBlue™ Pre-stained Protein Standard (Invitrogen, Carlsbad, CA), in kDa), Lanes (1) crude lysate, (2) flow through from amylose resin column, (3) undigested eluent from amylose resin (high volume), (4) TEV digested eluent from amylose resin (high volume), (5) undigested eluent from amylose resin (low volume), (6) TEV digested eluent from amylose resin (low volume), and (7) TEV digested eluent from amylose resin after Ni-NTA purification (high volume). MccH47-u/MccH47-MGE band is indicated with black arrows. MBP band indicated with green arrows. TEV indicated with a red arrow. High volume: 6 μL of protein sample. Low volume: 0.6 μL of protein sample. Novex® 16% Tricine gel from Thermo Fisher Scientific (Waltham, MA), denaturing conditions.

In particular, the MccH47 composition solutions were first analyzed and purified via polyacrylamide gel electro- phoresis (PAGE) followed by Mass Spectrometry (MS) MALDI-TOF. PAGE analysis clearly reveals a band corre- sponding to MccH47, post digestion with TEV, that is absent in the undigested sample (FIG. 3). MALDI-TOF analysis shows a monoisotopic peak at m/z=4971, corresponding to the presence of the unmodified peptide MccH47-u (account- ing for the additional serine residue, see above) as well as a second monoisotopic peak at m/z=5784 (FIG. 2B, FIG. 4), a difference in m/z of 813 which does not correspond to MccH47-MGDHBS$_{3/2/1}$, but instead corresponds to the mono-glycosylated cyclic enterobactin form MccH47- MGE.

Figure 4:
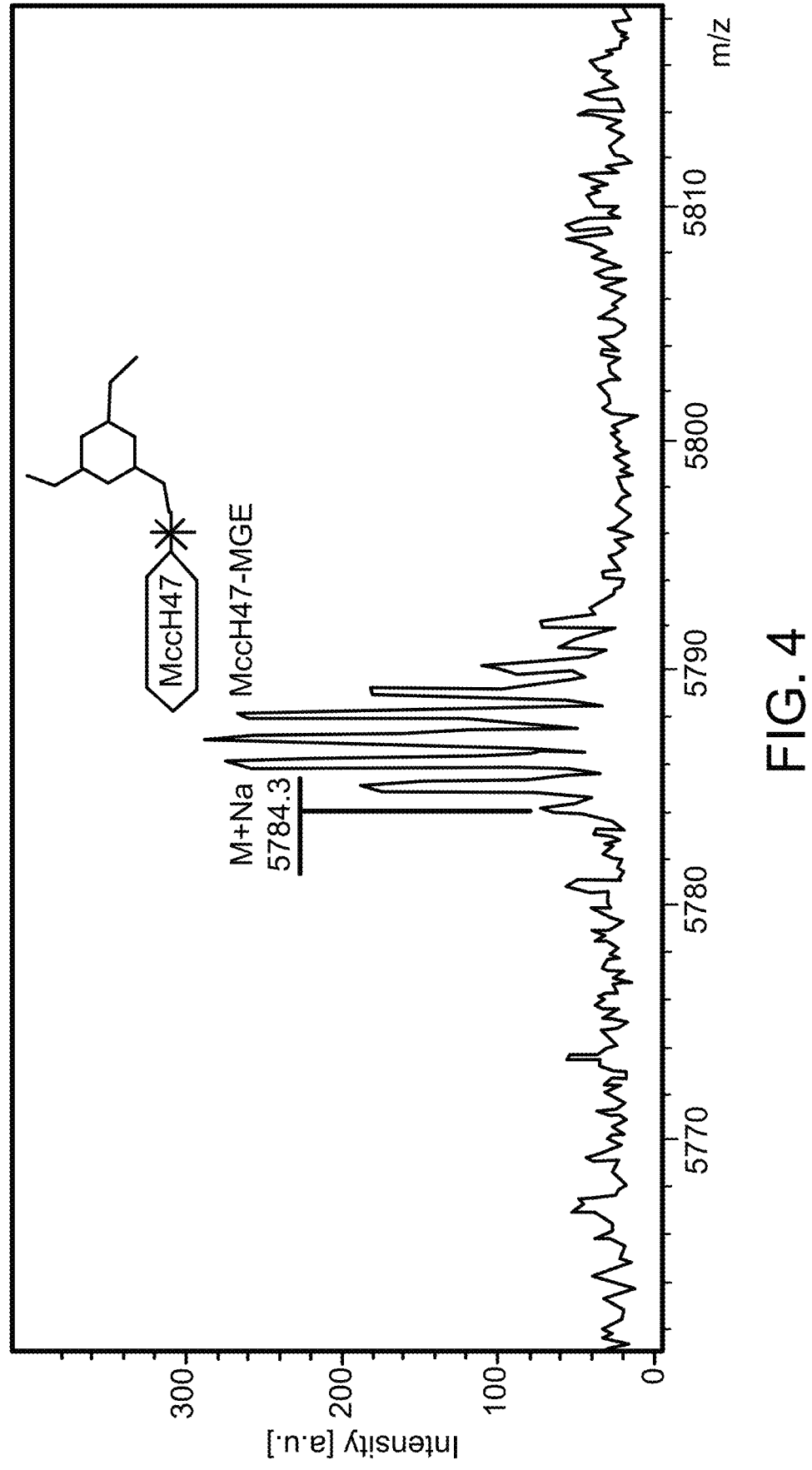
FIG. 4 is a graph of MALDI-TOF analysis of purified MccH47 with isotopic resolution showing peaks corresponding to MccH47-MGE with a monosodiated adduct. MccH47-MGE monoisotopic protein mass M=5761.5. Peaks labelled with m/z values correspond to the monoisotopic mass. (Na=Sodium)

For both MccH47-u and MccH47-MGE, there is an observed increase of 23 m/z units caused by monosodiated adducts on the protein (FIG. 4). Due to severe reduction in growth rate in strains overexpressing mchS1, we intention- ally omitted the enterobactin esterase from the design of pHMT-H47. We hypothesized that Fes, a native enterobactin esterase, would linearize enterobactin and remove DHBS subunits for detectable levels of MccH47-MGDHBS$_{3/2/1}$. However, in pHMT-H47, mchA, the enterobactin glucosyl- transferase, is constitutively expressed from a strong pro- moter, likely leading to elevated levels of MchA capable of rapidly glycosylating enterobactin.

Example 6: Phylogenetic Analysis

To determine if inhibitory properties would depend exclu- sively on the interaction with different F$_o$ subunits (A, B, C)

of the ATP synthase of the target strains[26], we built four phylogenetic trees (FIGS. 6A-6D) by aligning representative sequences of the target strains with respect to each $F_o$ subunit and the marker gene 16S rRNA (see Methods). For phylogenetic analysis, the nearly full length 16S rRNA sequence for the depicted strains was obtained from public data bases, a sequence alignment was generated using MEGA X39, and all samples were reduced to the length of the shortest aligned sequence. For the ATP synthase Fo subunits A, B and C, obtained amino acid sequences were aligned in MEGA X and utilized for tree building. A model test was used to estimate the best-fit substitution models for maximum likelihood phylogenetic analyses. The results are shown in FIGS. 6A-6D.

While subunit C does not show much variability between the different bacterial species (especially among Enterobacteriaceae), the subunits A and B roughly resemble the phylogenetic pattern of the 16S rRNA gene with one exception—while MccH47 susceptible *E. coli* and *Salmonella* are closely related with respect to $F_o$ similarity, the other genus strongly inhibited by MccH47, *P. mirabilis*, is more distant than non-susceptible strains including *E. cloacae, K. oxytoca* and *S. marcescens*.

Example 7: In Vivo Animal Testing

The MccH47-MGE composition as described herein is administered via oral gavage to antibiotic-treated mice that have been colonized with a high-dose of a multi-drug resistant bacteria demonstrated to be susceptible to the Mcch47-MGE composition.

The MccH47-MGE composition is administered as a single dose and/or as repeated doses on multiple subsequent days.

Multi-drug resistant bacteria abundance is estimated over time via sequencing and/or molecular methods.

Mice administered with the MccH47-MGE composition will show a significantly higher reduction in multi-drug resistant bacteria abundance compared to control mice receiving a placebo.

REFERENCES

All of which are Incorporated Herein by Reference in Their Entireties

1. Medina E, Pieper D H. Tackling Threats and Future Problems of Multidrug-Resistant Bacteria. In: Stadler M, Dersch P, editors. Overcome Antibiot Crisis [Internet]. Springer International Publishing; 2016 [cited 2017 Jun. 6]. p. 3-33. Available from: http://link.springer.com/chapter/10.1007/82_2016_492
2. CDC. Antibiotic Resistance Threats in the United States, 2013 [Internet]. 2013. Available from: https://www.cdc.gov/drugresistance/pdf/ar-threats-2013-508.pdf
3. Klemm E J, Shakoor S, Page A J, Qamar F N, Judge K, Saeed D K, Wong V K, Dallman T J, Nair S, Baker S, Shaheen G, Qureshi S, Yousafzai M T, Saleem M K, Hasan Z, Dougan G, Hasan R. Emergence of an Extensively Drug-Resistant *Salmonella enterica* Serovar *Typhi* Clone Harboring a Promiscuous Plasmid Encoding Resistance to Fluoroquinolones and Third-Generation Cephalosporins. mBio. 2018 Mar. 7; 9(1):e00105-18. PMID: 29463654
4. Jacobson A, Lam L, Rajendram M, Tamburini F, Honeycutt J, Pham T, Van Treuren W, Pruss K, Stabler S R, Lugo K, Bouley D M, Vilches-Moure J G, Smith M, Sonnenburg J L, Bhatt A S, Huang K C, Monack D. A Gut Commensal-Produced Metabolite Mediates Colonization Resistance to *Salmonella* Infection. Cell Host Microbe. 2018 08; 24(2):296-307.e7. PMCID: PMC6223613
5. Klemm E J, Wong V K, Dougan G. Emergence of dominant multidrug-resistant bacterial clades: Lessons from history and whole-genome sequencing. Proc Natl Acad Sci USA. 2018; 115(51):12872-12877.
6. Drider D, Rebuffat S. Prokaryotic Antimicrobial Peptides: From Genes to Applications. Springer Science & Business Media; 2011.
7. Granato E T, Meiller-Legrand T A, Foster K R. The Evolution and Ecology of Bacterial Warfare. Curr Biol CB. 2019; 29(11):R521-R537.
8. Jenssen H, Hamill P, Hancock R E. Peptide antimicrobial agents. Clin Microbiol Rev. 2006; 19(3):491-511.
9. Fjell C D, Hiss J A, Hancock R E, Schneider G. Designing antimicrobial peptides: form follows function. Nat Rev Discov. 2011; 11(1):37-51.
10. Patzer S I, Baquero M R, Bravo D, Moreno F, Hantke K. The colicin G, H and X determinants encode microcins M and H47, which might utilize the catecholate siderophore receptors FepA, Cir, Fiu and IroN. Microbiol Read Engl. 2003 September; 149(Pt 9):2557-2570. PMID: 12949180
11. Palmer J D, Piattelli E, McCormick B A, Silby M W, Brigham C J, Bucci V. Engineered Probiotic for the Inhibition of *Salmonella* via Tetrathionate-Induced Production of Microcin H47. ACS Infect Dis. 2017; (Journal Article).
12. Rodriguez E, Gaggero C, Lavina M. The structural gene for microcin H47 encodes a peptide precursor with antibiotic activity. Antimicrob Agents Chemother. 1999; 43(9):2176-2182.
13. Lavina M, Gaggero C, Moreno F. Microcin H47, a chromosome-encoded microcin antibiotic of *Escherichia coli*. J Bacteriol. 1990; 172(11):6585-6588.
14. Vassiliadis G, Destoumieux-Garzón D, Lombard C, Rebuffat S, Peduzzi J Isolation and Characterization of Two Members of the Siderophore-Microcin Family, Microcins M and H47. Antimicrob Agents Chemother. 2010 January; 54(1):288-297. PMCID: PMC2798501
15. Sassone-Corsi M, Nuccio S-P, Liu H, Hernandez D, Vu C T, Takahashi A A, Edwards R A, Raffatellu M. Microcins mediate competition among Enterobacteriaceae in the inflamed gut. Nature. 2016 Dec. 8; 540 (7632):280-283.
16. Poey M E, Azpiroz M F, Laviña M. Comparative analysis of chromosome-encoded microcins. Antimicrob Agents Chemother. 2006 April; 50(4):1411-1418. PMCID: PMC1426990
17. Azpiroz M F, Rodriguez E, Lavina M. The structure, function, and origin of the microcin H47 ATP-binding cassette exporter indicate its relatedness to that of colicin V. Antimicrob Agents Chemother. 2001; 45(3):969-972.
18. Winter S E, Thiennimitr P, Winter M G, Butler B P, Huseby D L, Crawford R W, Russell J M, Bevins C L, Adams L G, Tsolis R M, Roth J R, Bäumler A J. Gut inflammation provides a respiratory electron acceptor for *Salmonella*. Nature. 2010 Sep. 23; 467(7314):426-429. PMCID: PMC2946174
19. Azpiroz M F, Laviña M. Modular Structure of Microcin H47 and Colicin V. Antimicrob Agents Chemother. 2007 July; 51(7):2412-2419. PMCID: PMC1913283
20. Nolan E M, Walsh C T. Investigations of the MceIJ-catalyzed posttranslational modification of the microcin E492 C-terminus: linkage of ribosomal and nonribosomal peptides to form "trojan horse" antibiotics. Biochemistry. 2008; 47(35):9289-9299.

21. Azpiroz M F, Laviña M. Involvement of Enterobactin Synthesis Pathway in Production of Microcin H47. Antimicrob Agents Chemother. 2004 Apr. 1; 48(4):1235-1241. PMID: 15047525

22. Fischbach M A, Lin H, Liu D R, Walsh C T. In vitro characterization of IroB, a pathogen-associated C-glycosyltransferase. Proc Natl Acad Sci USA. 2005 Jan. 18; 102(3):571-576. PMCID: PMC545562

23. Lin H, Fischbach M A, Liu D R, Walsh C T. In vitro characterization of salmochelin and enterobactin trilactone hydrolases IroD, IroE, and Fes. J Am Chem Soc. 2005; 127(31):11075-11084.

24. Gaggero C, Moreno F, Laviña M. Genetic analysis of microcin H47 antibiotic system. J Bacteriol. 1993 Sep. 1; 175(17):5420-5427. PMID: 8366029

25. Rodriguez E, Lavina M. Genetic analysis of microcin H47 immunity. Can J Microbiol. 1998; 44(7):692-697.

26. Rodriguez E, Lavina M. The proton channel is the minimal structure of ATP synthase necessary and sufficient for microcin h47 antibiotic action. Antimicrob Agents Chemother. 2003; 47(1):181-187.

27. Trujillo M, Rodríguez E, Laviña M. ATP Synthase Is Necessary for Microcin H47 Antibiotic Action. Antimicrob Agents Chemother. 2001 Nov. 1; 45(11):3128-3131. PMID: 11600367

28. Zheng T, Bullock J L, Nolan E M. Siderophore-mediated cargo delivery to the cytoplasm of Escherichia coli and Pseudomonas aeruginosa: syntheses of monofunctionalized enterobactin scaffolds and evaluation of enterobactin-cargo conjugate uptake. J Am Chem Soc. 2012; 134 (44):18388-18400.

29. Hara S, Yamakawa M. Production in Escherichia of moricin, a novel type antibacterial peptide from the silkworm, Bombyx mori. Biochem Biophys Res Commun. 1996; 220(3):664-669.

30. Bantysh O, Serebryakova M, Makarova K S, Dubiley S, Datsenko K A, Severinov K. Enzymatic synthesis of bioinformatically predicted microcin C-like compounds encoded by diverse bacteria. mBio. 2014; 5(3):e01059-14.

31. Delgado M A, Vincent P A, Farías R N, Salomón R A. Yoj I of Escherichia coli functions as a microcin J25 efflux pump. J Bacteriol. 2005 May; 187(10):3465-3470. PMCID: PMC1112001

32. Hoerr V, Duggan G E, Zbytnuik L, Poon K K H, Große C, Neugebauer U, Methling K, Löffler B, Vogel H J. Characterization and prediction of the mechanism of action of antibiotics through NMR metabolomics. BMC Microbiol. 2016 May 10; 16(1):82.

33. Chao L, Levin B R. Structured habitats and the evolution of anticompetitor toxins in bacteria. Proc Natl Acad Sci USA. 1981; 78(10):6324-6328.

34. Shapiro J A, Wencewicz T A. Acinetobactin Isomerization Enables Adaptive Iron Acquisition in Acinetobacter baumannii through pH-Triggered Siderophore Swapping. ACS Infect Dis. 2016; 2(2):157-168.

35. Isabella V M, Ha B N, Castillo M J, Lubkowicz D J, Rowe S E, Millet Y A, Anderson C L, Li N, Fisher A B, West K A, Reeder P J, Momin M M, Bergeron C G, Guilmain S E, Miller P F, Kurtz C B, Falb D. Development of a synthetic live bacterial therapeutic for the human metabolic disease phenylketonuria. Nat Biotechnol. 2018 September; 36(9):857-864.

36. Gibson D G, Young L, Chuang R-Y, Venter J C, Hutchison C A, Smith H O. Enzymatic assembly of DNA molecules up to several hundred kilobases. Nat Methods. 2009 May; 6(5):343-345.

37. Saiki R K, Gelfand D H, Stoffel S, Scharf S J, Higuchi R, Horn G T, Mullis K B, Erlich H A. Primer-directed enzymatic amplification of DNA with a thermostable DNA polymerase. Science. 1988; 239(4839):487-491.

38. Wycuff D R, Matthews K S. Generation of an AraC-araBAD promoter-regulated T7 expression system. Anal Biochem. 2000 Jan. 1; 277(1):67-73. PMID: 10610690

39. Jacob D. Palmer, Benedikt M. Mortzfeld, Emma Piattelli, Mark W. Silby, Beth A. McCormick, and Vanni Bucci Microcin H47: A Class IIb Microcin with Potent Activity Against Multidrug Resistant Enterobacteriaceae. ACS Infect. Dis. 2020, 6, 4, 672-679

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated and purified microcin-mono-glycosylated cyclic enterobactin (microcin-MGE) composition comprising a class IIb microcin covalently linked at the C-terminus via a single glycosyl molecule to a cyclic enterobactin.

2. The composition of claim 1, wherein the microcin-MGE composition comprises an MccH47-MGE, MccI47-MGE, MccE492-MGE, MccM-MGE, or MccG492-MGE composition.

3. The composition of claim 1, wherein the microcin-MGE composition comprises an MccH47-MGE composition or an MccI47-MGE composition.

4. The composition of claim 1, further comprising a pharmaceutically acceptable carrier comprising one or more of a solvent, dispersion media, coating, antibacterial agent, isotonic and absorption delaying agent, buffer, excipient, binder, lubricant, gel, or a surfactant.

5. A method of treating a subject for intestinal dysbiosis or a bacterial infection, the method comprising:
   identifying a subject as having intestinal dysbiosis or a bacterial infection; and
   administering to the subject a therapeutically effective amount of a microcin-MGE composition of claim 1.

6. The method of claim 5, wherein the subject is a human and the composition is administered by endoscopy, enteroscopy, colonoscopy, a nasoduodenal catheter, enema, or orally.

7. The method of claim 5, wherein the bacterial infection is a gram-negative bacterial infection.

8. The method of claim 7, wherein the bacterial infection is carbapenem-resistant Enterobacteriaceae infection, Campylobacter infection, E. coli infection, Salmonella infection, Shigella infection and/or Yersinia infection.

9. A method of reducing a risk of a bacterial infection, the method comprising:
   identifying a subject as having a risk of a bacterial infection; and
   administering to the subject a prophylactically effective amount of a microcin-MGE composition of claim 1.

10. The method of claim 9, wherein the subject is a human and is administered one or more antibiotics.

* * * * *